(12) United States Patent
Bartel et al.

(10) Patent No.: US 11,011,603 B2
(45) Date of Patent: May 18, 2021

(54) PREPARATION OF NANOCRYSTALS WITH MIXTURES OF ORGANIC LIGANDS

(71) Applicant: Life Technologies Corporation, Carlsbad, CA (US)

(72) Inventors: Joseph Bartel, Eugene, OR (US); Yongfen Chen, Eugene, OR (US); Noah Lermer, Eugene, OR (US); Timothy Carter, Eugene, OR (US); Scott Sweeney, Eugene, OR (US); Chad Teters, Eugene, OR (US); Wenxi Huang, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 16/107,903

(22) Filed: Aug. 21, 2018

(65) Prior Publication Data

US 2019/0074354 A1 Mar. 7, 2019

Related U.S. Application Data

(62) Division of application No. 13/976,621, filed as application No. PCT/US2011/067144 on Dec. 23, 2011, now Pat. No. 10,224,398.

(60) Provisional application No. 61/427,760, filed on Dec. 28, 2010, provisional application No. 61/441,579, filed on Feb. 10, 2011.

(51) Int. Cl.
| | |
|---|---|
| *G01N 33/58* | (2006.01) |
| *H01L 29/06* | (2006.01) |
| *B82Y 30/00* | (2011.01) |
| *C30B 7/00* | (2006.01) |
| *C30B 29/40* | (2006.01) |
| *C30B 29/48* | (2006.01) |
| *C30B 29/60* | (2006.01) |
| *G01N 33/533* | (2006.01) |
| *H01L 51/00* | (2006.01) |
| *H01L 21/02* | (2006.01) |
| *H01L 31/0352* | (2006.01) |
| *H01L 33/04* | (2010.01) |
| *B82Y 40/00* | (2011.01) |
| *B82Y 20/00* | (2011.01) |

(52) U.S. Cl.
CPC .......... *H01L 29/0665* (2013.01); *B82Y 30/00* (2013.01); *C30B 7/00* (2013.01); *C30B 29/40* (2013.01); *C30B 29/48* (2013.01); *C30B 29/60* (2013.01); *G01N 33/533* (2013.01); *G01N 33/588* (2013.01); *H01L 21/02628* (2013.01); *H01L 31/035209* (2013.01); *H01L 33/04* (2013.01); *H01L 51/0007* (2013.01); *B82Y 20/00* (2013.01); *B82Y 40/00* (2013.01)

(58) Field of Classification Search
CPC ......... H01L 29/0665; H01L 31/035209; H01L 33/04; H01L 21/02628; H01L 51/0007; G01N 33/588; G01N 33/533; B82Y 20/00; B82Y 40/00; B82Y 30/00; Y02E 10/549; C30B 7/00; C30B 29/40; C30B 29/48; C30B 29/60; C30B 11/00

See application file for complete search history.

(56) References Cited

U.S. PATENT DOCUMENTS

| | | |
|---|---|---|
| 5,262,357 A | 11/1993 | Alivisatos et al. |
| 5,505,928 A | 4/1996 | Alivisatos et al. |
| 5,690,807 A | 11/1997 | Clark, Jr. et al. |
| 5,990,479 A | 11/1999 | Weiss et al. |
| 6,048,616 A | 4/2000 | Gallagher et al. |
| 6,207,229 B1 | 3/2001 | Bawendi et al. |
| 6,207,299 B1 | 3/2001 | Krauth et al. |
| 6,322,901 B1 | 11/2001 | Bawendi et al. |
| 6,576,291 B2 | 6/2003 | Bawendi et al. |
| 6,649,138 B2 | 11/2003 | Adams et al. |
| 6,727,065 B2 | 4/2004 | Weiss et al. |
| 6,815,064 B2 | 11/2004 | Treadway et al. |
| 7,147,712 B2 | 12/2006 | Zehnder et al. |
| 7,253,452 B2 | 8/2007 | Steckel et al. |
| 7,288,468 B2 | 10/2007 | Jang et al. |
| 7,615,800 B2 | 11/2009 | Kahen |
| 7,767,260 B2 | 8/2010 | Peng et al. |
| 7,935,419 B1 | 5/2011 | Hollingsworth et al. |
| 8,404,154 B2 | 3/2013 | Breen et al. |
| 8,637,082 B2 * | 1/2014 | Tulsky .................. B82Y 30/00 424/489 |
| 9,181,472 B2 * | 11/2015 | Bartel ................. C09K 11/025 |
| 9,577,037 B2 | 2/2017 | Welch et al. |
| 10,084,042 B2 | 9/2018 | Welch et al. |
| 2003/0136943 A1 | 7/2003 | Alivisatos et al. |
| 2006/0057382 A1 | 3/2006 | Treadway et al. |

(Continued)

FOREIGN PATENT DOCUMENTS

| | | |
|---|---|---|
| CN | 1595673 A | 3/2005 |
| EP | 1516944 A1 * | 3/2005 |

(Continued)

OTHER PUBLICATIONS

Wang et al. ("Ligand Control of Growth Morphology and Capping Strcuture of Colloidal CdSe Nanorods", Chem. Mater. vol. 2007, vol. 19, pp. 2573-2580 (Year: 2007).*

(Continued)

*Primary Examiner* — Tracy Vivlemore
*Assistant Examiner* — Nam P Nguyen

(57) ABSTRACT

Semiconductor nanocrystals prepared using a mixture of organic ligands (e.g., oxoacids), as well as compositions, kits, and methods of using such semiconductor nanocrystals are disclosed.

15 Claims, 6 Drawing Sheets

(56) References Cited

U.S. PATENT DOCUMENTS

| | | |
|---|---|---|
| 2006/0157720 A1 | 7/2006 | Bawendi et al. |
| 2007/0289491 A1 | 12/2007 | Peng et al. |
| 2008/0138514 A1 | 6/2008 | Jang et al. |
| 2008/0220593 A1 | 9/2008 | Pickett et al. |
| 2008/0280223 A1 | 11/2008 | Levy et al. |
| 2010/0062154 A1 | 3/2010 | Shin et al. |
| 2010/0163800 A1 | 7/2010 | Peng et al. |
| 2010/0308271 A1 | 12/2010 | Bartel |
| 2012/0157824 A1 | 6/2012 | Bossmann et al. |

FOREIGN PATENT DOCUMENTS

| | | |
|---|---|---|
| EP | 1980652 A2 | 10/2008 |
| WO | WO-9926299 A1 | 5/1999 |
| WO | WO-0029617 A2 | 5/2000 |
| WO | WO-2008127378 A2 | 10/2008 |
| WO | WO-2009025913 A2 * | 2/2009 |
| WO | WO-2009136974 A2 | 11/2009 |
| WO | WO-2010002540 A2 | 1/2010 |
| WO | WO-2010039897 A2 | 4/2010 |
| WO | WO-2010040074 A2 | 4/2010 |
| WO | WO-2010040109 A2 | 4/2010 |
| WO | WO-2010040111 A2 | 4/2010 |
| WO | WO-2010048580 A2 | 4/2010 |
| WO | WO-2010048581 A2 | 4/2010 |
| WO | WO-2010096084 A1 | 8/2010 |
| WO | WO-2011100023 A1 | 8/2011 |
| WO | WO-2011123349 A1 | 10/2011 |
| WO | WO-2012027203 A1 | 3/2012 |
| WO | WO-2012092178 A1 | 7/2012 |
| WO | WO-2012092195 A1 | 7/2012 |

OTHER PUBLICATIONS

English partial translation of Zhixian Gao et al. "Nano Biomedicine," Chemical Industry Press, Jan. 2007, pp. 143-147. (Year: 2007).*

Aharoni, A. et al., "Synthesis of InAs/CdSe/ZnSe Core/Shell1/Shell2 Structures with Bright and Stable Near-Infrared Fluorescence", J. Am. Chem. Soc., vol. 128 (1), 2006, 257-264.

Alivisatos, A. , "Semiconductor Clusters, Nanocrystals, and Quantum Dots", 271, 1996, 933-937.

Bruchez, Marcel P. et al., "Luminescent Semiconductor Nanocrystals: Intermitten Behaviour and Use as Fluorescent Biological Probes", UMI Disseratation Information Service, 1998, 1-115.

Chen, Yongfen et al., ""Giant" Multishell CdSe Nanocrystal Quantum Dots with Suppressed Blinking", J. Am. Chem. Soc., 130 (15), 2008, 5026-5027.

Coffer, Jeffery L. et al., "Characterization of quantum-confined CdS nanocrystallites stabilized by deoxyribonucleic acid (DNA)", Nanotechnology, vol. 3, 1992, 69-76.

Dabbousi, B. O. et al., "(Cdse)Zns Core-Shell Quantum Dots: Synthesis and Characterizations of a Size Series of Highly Luminescent Nanocrystallites", J. Phys. Chem. B, vol. 101, No. 46, Jun. 26, 1997, 9463-9475.

Danek, M. et al., "Preparation of II-VI quantum dot composites by electrospray organometallic chemical vapor deposition", J. Crvst. Growth 145 Issues 1-4 1994, 714-720.

Efros, A. et al., "Band-edge exciton in quantum dots of semiconductors with a degenerate valence band: dark and bright exciton 4856 states", Physical Review B. vol. 54, Issue 7, 1996, 4843-4856.

EP 11853691.1, , "Supplementary European Search Report dated", Nov. 13, 2014, 9 Pages.

EP 11854051.7, , "Supplementary European Search Report dated", Dec. 3, 2014, 8 Pages.

Evans, Christopher et al., "Mysteries of TOPSe Revealed: Insights into Quantum Dot Nucleation", J. Am. Chem. Soc., 132, 2010, 10973-10975.

Extended European Search Report for Application No. 18152936.3, dated Sep. 13, 2018, 13 pages.

Forster, T., "Intermolecular energy migration and fluorescence", Annalen der Physik, vol. 437(1-2), 1948, 55-75.

Galland, Christophe et al., "Two Types of Luminescenece Blinking Revealed by Spectroelectrochemistry of Single Quantum Dots", Nature, vol. 479, Nov. 2011, 203-208.

Garcia-Santamaria , Florencio et al., "Suppressed Auger Recombination in "Giant" Nanocrystals Boosts Optical Gain Performance", Nano Lett., 9 (10), 2009, 3482-3488.

Grabolle, M et al., "Stability and Fluorescence Quantum Yield of CdSe—ZnS Quatum Dots—Influence of the Thickness of the ZnS Shell", Ann. N. Y. Acad. Sci, 1130, 2008, 235-241.

Greytak, A. et al., "Alternating layer addition approach to CdSe/CdS core/shell quantum dots with near-unity quantum yield and high on-time fractions", Chem. Sci. vol. 3, 2012, pp. 2028-2034.

Hines, M. et al. "Synthesis and Characterization of Strongly Luminescing ZnS-Capped CdSe Nanocrystals", J. Phys. Chem. vol. 100, No. 2, 1996 , 468-471.

Hyldahl, M. et al., "Photo-stability and performance of CdSe/ZnS quantum dots in luminescent solar concentrators", Solar Energy 83 available on-line Nov. 12, 2008, 2009,.

Ivanov, et al., "Typed-II Core/Shell CdS/ZnSe Nanocrystals: Synthesis, Electronic Structures, and Spectroscopic Properties", J. Am. Chem. Soc., 2005, 11708-11719.

Kortan, A. R. et al., "Nucleation and growth of Cdse on ZnS Quantum crystallite seeds, and vice versa, in inverse Micelle Media.", J. Am. Chem. Soc., vol. 112, 1990, 1327-1332.

Kuno, M: et al., The Band Edge Luminescence of Surface Modified CDSE Nanocrystallites Probing the Luminescence State>>, Journal of Chemical Physics, American Institute of Physics, New York, NY, vol. 1. 106, No. 23, 1997, 9869-9882.

Lakowicz, J. R., "Energy Transfer", Principles of Fluorescence Spectroscopy, 2nd Ed.Plenum Publishing Corp. New York, NY, 1999, 367-394.

Mahler, B. et al., "Towards non-blinking colloidal quantum dots", Nature Materials, vol. 7, 2008, pp. 659-664.

McBride, J. et al., "Structural Basis for Near Unity Quantum Yield Core/Shell Nanostructures", Nano Letters, vol. 6, No. 7, 2006, 1496-1501.

Molecular Probes, "Product sheet for Qdot.RTM. 625 Streptavidin Conjugates", 2007, pp. 1-15.

Murray, C. B. et al., "Synthesis and characterization of nearly monodisperse CdE (E=sulfur, selenium, tellurium) semiconductor nanocrystallites" Journal of the American Chemical Society, vol. 115, No. 19, 1993, 8706-8715.

Nirmal, Manoj et al., "Luminescence Photophysics in Semiconductor Nanocrystals", Ace. Chem. Res. 32 (5). 1999, 407-414.

PCT/US11 /67174, , "International Search Report", dated May 4, 2012, pp. 1-4.

PCT/US11/67144, "Written Opinion", dated Apr. 27, 2012, pp. 1-11.

PCT/US11/67174, , "Written Opinion", dated May 4, 2012, pp. 1-11.

PCT/US2011/067144, , "International Search Report dated", Apr. 27, 2012, 4 Pages.

Peng et al. (1997), "Epitaxial Growth of Highly Luminescent CdSe/CdS Core/Shell Nanocrystals with Photostability and Electronic Accessibility," J. Am. Chem. Soc. 119(30):7019-7029.

Premachandran, et al., ""The Enzymatic Synthesis of Thiol-Containing Polymers to prepare Polymer-Cds Nanocomposites"", Chem. Mater. 9(6), 1997, 1342-1347.

Qu, Lianhua et al., "Alternative Routes Toward High Quality CdSe Nanocrystals", Nano Letters vol. 1 No. 6 2001, 333-337.

Reiss, Peter et al., "Core/Shell Semiconductor Nanocrystals", vol. 5 (2). 2009, 154-158.

Rosenthal, S. et al., "Synthesis, surface studies, composition and structural characterization of CdSe, core/shell and biologically active nanocrystals", Surface Science Reports, vol. 62, 2007, 111-157.

Talapin, D. et al., "Seeded Growth of Highly Luminescent CdSe/CdS Nanoheterostructures with Rod and Tetrapod Morphologies", Nano Letters, vol. 7, No. 10, 2007, 2951-2959.

Wang, Fudong et al., "Spectroscopic Identification of Tri-n-octylphosphine Oxide (TOPO) Impurities and Elucidation of Their

(56) References Cited

OTHER PUBLICATIONS

Roles in Cadmium Selenide Quantum-Wire Growth", Department of Chemistry, Washington University, Jan. 14, 2009, 1-38.

Wang, Fudong et al., "The Trouble with TOPO; Identification of Adventitious Impurities Beneficial to the Growth of Cadmium Selenide Quantum Dots, Rods, and Wires", Nano. Lett., 8(10), 2008, 3521-3524.

Xie et al., Synthesis and Characterization of Highly Luminescent CdSe-Core CdS/Zn0.5Ce0.5S/ZnS Multishell Nanocrystals, published on the web, Apr. 29, 2005, J. Am. Chem. Soc., vol. 127, pp. 7480-7488.

Yu, W. William et al., "Experimental Determination of the Extinction Coefficient of CdTe, CdSe, and CdS Nanocrystals", Chem. Mater., 15 (14), 2003, 2854-2860.

Zhong, Xinhua et al., "Composition-Turnable, ZnxCd1-xSe Nanocrystals with High Luminescence and stability", Journal of the American Chemical Society vol. 125, No. 28 Jun. 21, 2003, 8589-8594.

Hamid Reza Rajabi et al: "Study of capping agent effect on the structural, optical and photocatalytic properties of zinc sulfide quantum dots", Materials Science in Semiconductor Processing, vol. 48, Jun. 1, 2016 (Jun. 1, 2016), pp. 14-22, XP055676569, UK, ISSN: 1369-8001, DOI:10.1016/j.mssp.2016.02.021.

Zhixian Gao, et al., "Nano Biomedicine," Chemical Industry Press, Jan. 2007, pp. 143-147.

\* cited by examiner

PREPARATION OF NANOCRYSTALS WITH MIXTURES OF ORGANIC LIGANDS

CROSS REFERENCE TO RELATED APPLICATIONS

This application is a Division of U.S. Non-Provisional application Ser. No. 13/976,621, filed Jun. 27, 2013, which is a 371 National Stage Application of PCT/US11/67144, filed Dec. 23, 2011, which claims the benefit under 35 U.S.C. § 119(e) of U.S. Provisional Application No. 61/427,760, filed Dec. 28, 2010, and U.S. Provisional Application No. 61/441,579, filed Feb. 10, 2011, the disclosures of which are hereby incorporated by reference as if set forth in full.

TECHNICAL FIELD

The invention relates to semiconductor nanocrystals prepared using a mixture of organic ligands.

BACKGROUND

Semiconductor nanocrystals (also referred to as "quantum dots") with small diameters can have properties intermediate between molecular and bulk forms of matter. Small diameter semiconductor materials can exhibit quantum confinement of both the electron and hole in three dimensions. Quantum confinement plays a key role in determining the size-dependent optical properties of semiconductor nanocrystals. One effect of quantum confinement is an increase in the effective band gap of the material with decreasing nanocrystal size. As the size of the semiconductor nanocrystal decreases, both the optical absorption and fluorescence emission of the nanocrystals shift to higher energy (i.e., to the blue). The extinction coefficient of the nanocrystal is also size-dependent. As the size of a nanocrystal increases, the extinction coefficient of the particle increases in a non-linear fashion. Consequently, for a given material, larger semiconductor nanocrystals are typically brighter than smaller nanocrystals on a per mole basis.

The quantum yield (QY) is an important measure for determining the quality of any given population of fluorescent semiconductor nanocrystals. A high quantum yield can indicate that some or all of these potential non-irradiative pathways are absent in the collection of quantum dots sampled. There are numerous mechanisms by which the fluorescence of a quantum dot can diminish or the quantum dot can become non-fluorescent (e.g., surface trap states, crystalline defects, photochemical effects, and the like). Many ways of improving the quantum yield of quantum dots have been proposed. In one approach to enhance quantum yield, nanocrystals can include a semiconductor core and a passivating layer. The passivating layer can be formed of organic compounds (also referred to as "ligands") such as amines that coordinate to atoms in the core material. Yet other approaches utilize semiconductor shell materials with bandgaps higher than those of the core materials. Semiconductor shells can minimize deep-trap emission sites and thereby enhance the quantum yield and stability of the nanocrystal particle. Methods involving the use of organic ligands to improve the quantum yield in organic solution do little to enhance quantum yield in aqueous solution, while inorganic shells can improve the quantum yield in both organic and aqueous solution. Consequently, most recent advances in the field have moved in this direction. Despite the materials and methods available to prepare nanocrystals, there exists a need for new materials and methods to improve the organic and aqueous quantum yields of semiconductor nanocrystals.

SUMMARY

Provided herein are novel semiconductor nanocrystal compositions, kits, and methods for preparing and using these compositions.

In one aspect, a method for producing a population of semiconductor nanocrystals is provided including:

combining a plurality of semiconductor nanocrystal cores, at least one solvent, a first semiconductor shell precursor, and a second semiconductor shell precursor, wherein the first and second semiconductor shell precursors are different, and at least two different oxoacid compounds to provide a reaction mixture;

heating the reaction mixture for a period of time sufficient to induce formation of a semiconductor shell layer on at least one core, thereby producing a population of semiconductor nanocrystals.

In certain aspects, the method can include:

first combining the plurality of semiconductor nanocrystal cores with the at least one solvent and the at least two different oxoacid compounds; and then adding the first and second semiconductor shell precursors.

In other aspects, the method can include:

first combining the plurality of semiconductor nanocrystal cores with the at least one solvent; and then adding the first and second semiconductor shell precursors and the at least two different oxoacid compounds.

In yet another aspect, a method for producing a population of semiconductor nanocrystals is provided that includes:

combining a plurality of semiconductor nanocrystal cores, wherein each core has an aspect ratio of greater than 1:1, at least one solvent, a first semiconductor shell precursor, and a second semiconductor shell precursor, wherein the first and second semiconductor shell precursors are different, and at least two oxoacid compounds to provide a reaction mixture; and heating the reaction mixture for a period of time sufficient to induce formation of a semiconductor shell layer on at least one core, wherein the aspect ratio of the core-shell nanocrystal is less than the aspect ratio of the nanocrystal core, thereby producing a population of semiconductor nanocrystals.

In yet another aspect, the production methods provided herein can include adding the first and second shell precursors alternately in layer additions.

Any of the methods provided herein can further include applying a hydrophilic overcoating to each semiconductor nanocrystal in the population that renders the nanocrystal dispersible in an aqueous medium.

Representative oxoacid compounds that can used in the methods provided herein include phosphonic acid compounds, phosphinic acid compounds, carboxylic acid compounds, sulfonic acid compounds, boronic acid compounds, and derivatives (e.g., conjugate bases and esters) and combinations thereof. In certain embodiments, the at least two oxoacid compounds can include at least two different alkylphosphonic acid compounds. For example, the at least two oxoacid compounds can include at least two different $C_1$-$C_{20}$ alkylphosphonic acid compounds. The at least two oxoacid compounds can include a first compound selected from $C_1$-$C_{10}$ alkylphosphonic acid compounds and a second compound selected from $C_{10}$-$C_{20}$ alkylphosphonic acid compounds. In certain embodiments, at least one oxoacid compound can be methylphosphonic acid, ethylphosphonic acid, butylphosphonic acid, hexylphosphonic acid, or octylphosphonic acid. In certain embodiments, at least one oxoacid compound is tetradecylphosphonic acid (TDPA). In some embodiments, the at least two oxoacid compounds can include tetradecylphosphonic acid and at least one $C_1$-$C_{10}$ alkylphosphonic acid compound. For example, the at least two oxoacid compounds can include tetradecylphosphonic acid and a phosphonic acid selected from methylphosphonic acid, ethylphosphonic acid, butylphosphonic acid, hexylphosphonic acid, and octylphosphonic acid. In certain embodiments, the at least two oxoacid compounds include tetradecylphosphonic acid and ethylphosphonic acid. In certain embodiments, the at least two oxoacid compounds can include at least two carboxylic acid compounds. For example, at least one of the two different oxoacid compounds can be selected from the group consisting of $C_{10}$-$C_{20}$ carboxylic acids, and at least one of the two different oxoacid compounds is selected from $C_1$-$C_{10}$ carboxylic acids. The at least one of the two different oxoacid compounds can be selected from the group consisting of lauric acid, myristic acid, palmitic acid, and stearic acid, and at least one of the two different oxoacid compounds is selected from the group consisting of acetic acid, propionic acid, butyric acid, hexanoic acid, and octanoic acid.

In yet another aspect, the at least two different oxoacid compounds can have at least two different molecular weights. For example, the at least two oxoacid compounds can include a first oxoacid compound and a second oxoacid compound, wherein the first and second oxoacid compounds have two different molecular weights. The mole fraction of the lower molecular weight oxoacid compound relative to the total number of moles of oxoacid compounds can range from about 0.1% to about 99.9%. The mole fraction of the lower molecular weight oxoacid compound relative to the total number of moles of oxoacid compounds can be greater than about 0.5%; or greater than about 1%; or greater than about 5%; or greater than about 10%; or greater than about 15%. In certain embodiments, the mole fraction of the lower molecular weight oxoacid compound relative to the total number of moles of oxoacid compounds is greater than about 0.5%. In some embodiments, the mole fraction is greater than about 2%. In some embodiments, the mole fraction is greater than about 5%. In certain embodiments, the mole fraction of the lower molecular weight oxoacid compound relative to the total number of moles of oxoacid compounds is about 1% to about 10%; or about 1% to about 15%; or about 1% to about 20%. In certain embodiments, the mole fraction of the lower molecular weight oxoacid compound relative to the total number of moles of oxoacid compounds is about 0.5% to about 20%; or about 2% to about 20%; or about 5% to about 15%. In certain embodiments, the at least two oxoacid compounds include two phosphonic acid compounds, having different molecular weights, wherein the mole fraction of the lower molecular weight oxoacid compound relative to the total number of moles of oxoacid compounds is about 0.5% to about 20%.

In certain embodiments, the at least two oxoacid compounds can include two phosphonic acid compounds having two different molecular weights, wherein the mole fraction of the lower molecular weight phosphonic acid is greater than about 2%; or greater than about 5%; or greater than about 10%. In certain embodiments, the at least two oxoacid compounds can include two phosphonic acid compounds having two different molecular weights, wherein the mole fraction of the lower molecular weight phosphonic acid is about 1% to about 10%; or about 1% to about 20%.

The methods provided herein can utilize any type of suitable semiconductor nanocrystal core. For example, the core can include a Group II-VI, Group II-VI-VI, Group III-V, Group III-III-V, Group III-V-V or a Group semiconductor material. In some embodiments, the nanocrystal core having an aspect ratio of 1:1 or greater. In certain embodiments, the aspect ratio is about 1:1 (i.e., spherical or nearly spherical). In other embodiments, the aspect ratio is greater than about 1:1. In certain embodiments, each nanocrystal core has an aspect ratio of about 1:5 to about 3.0.

The methods described herein utilize a first and second semiconductor shell precursor. The first semiconductor shell precursor can include one or more Group 2, 12, 13 and 14 element-containing compounds. The second semiconductor shell precursor can include one or more Group 2, 12, 13, 14, 15 and 16 element-containing compounds.

The methods described herein can utilize a solvent selected from amines, alkyl phosphines, alkyl phosphine oxides, fatty acids, ethers, furans, phospho-acids, pyridines, alkenes, alkynes and combinations thereof.

In another aspect, a population of semiconductor nanocrystals is provided that is produced by any one of the methods described herein.

In yet another aspect, provided herein is a population of semiconductor nanocrystals, wherein each nanocrystal in the population includes:
  a) a semiconductor core;
  b) a semiconductor shell layer disposed on the semiconductor core; and
  c) at least two different oxoacid compounds.

In certain aspects, the semiconductor core includes an external semiconductor shell layer. In some aspects, the at least two different oxoacid compounds are disposed on the semiconductor shell layer.

The core of the semiconductor nanocrystal can include a Group II-VI, Group II-VI-VI, Group III-V, Group III-III-V, Group III-V-V or a Group semiconductor material. The semiconductor core can be spherical, nearly spherical or elongated and can have an aspect ratio of about 1:1 or greater. In some embodiment, the semiconductor core has an aspect ratio of about 1:1. In other embodiments, the core has an aspect ratio of about 1.2:1 to about 10:1. The semiconductor shell layer can include a Group II-VI, a Group II-VI-VI, Group III-V, Group III-III-V, Group III-V-V or a Group semiconductor material. Typically, the shell semiconductor material differs from the semiconductor core material. The core-shell nanocrystal in the population can have an aspect ratio of about 1:1 or greater. In some embodiments, the nanocrystal has an aspect ratio of about 1:1 (i.e., spherical or nearly spherical). In other embodiments, the nanocrystal has an aspect ratio of about 1.2:1 to about 10:1 (e.g., elongated or rod-shaped).

In yet another aspect, populations are provided that include at least two different oxoacid compounds comprise a first oxoacid compound and a second oxoacid compound, wherein the first and second oxoacid compounds have different molecular weights. In certain embodiments, the mole fraction of the lower molecular weight oxoacid compound relative to the total number of moles of oxoacid compounds is greater than about 0.5%. In other embodiments, the mole fraction of the lower molecular weight oxoacid compound relative to the total number of moles of oxoacid compounds is greater than about 2%. In yet other embodiments, the mole fraction of the lower molecular weight oxoacid compound relative to the total number of moles of oxoacid compounds is greater than about 5%. In yet another embodiments, the mole fraction of the lower molecular weight oxoacid compound relative to the total number of moles of oxoacid compounds is about 0.5% to about 20%. In yet another embodiments, the mole fraction of the lower molecular weight oxoacid compound relative to the total number of moles of oxoacid compounds is about 2% to about 20%. In yet another embodiment, the mole fraction of the lower molecular weight oxoacid compound relative to the total number of moles of oxoacid compounds is about 5% to about 15%.

The at least two different oxoacid compounds can be selected from the group consisting of phosphonic acid compounds, phosphinic acid compounds, sulfonic acid compounds, boronic acid compounds, carboxylic acid compounds, and derivatives and combinations thereof. The at least two different oxoacid compounds can include two phosphonic acid compounds of different molecular weight. The at least two oxoacid compounds can include at least two different alkylphosphonic acid compounds. The at least two oxoacid compounds can include at least two different $C_1$-$C_{20}$ alkylphosphonic acid compounds. The at least two different oxoacid compounds can include a first phosphonic acid compound selected from $C_1$-$C_{10}$ alkylphosphonic acid compounds and a second phosphonic acid compound selected from $C_{10}$-$C_{20}$ alkylphosphonic acid compounds. The at least one of the oxoacid compounds is tetradecylphosphonic acid. The at least one of the oxoacid compounds can be methylphosphonic acid, ethylphosphonic acid, butylphosphonic acid, hexylphosphonic acid or octylphosphonic acid. The at least two different oxoacid compounds include tetradecylphosphonic acid and a $C_1$-$C_{10}$ alkylphosphonic acid. In certain embodiments, the at least two different oxoacid compounds include tetradecylphosphonic acid and ethylphosphonic acid.

In yet another aspect, each nanocrystal in the population can further include a hydrophilic overcoating on the semiconductor shell layer that renders the nanocrystal dispersible in an aqueous medium. In certain aspects, a water-dispersible nanocrystal is provided that is associated with a biological molecule, cell, or drug.

The populations of nanocrystals provided herein can emit fluorescence over a range of wavelengths and can exhibit superior optical properties. The nanocrystal populations provided herein can exhibit a quantum yield of greater than about 60%; or greater than about 65%; or greater than about 70%; or greater than about 75%; or greater than about 80% when measured in an organic or an aqueous medium. In certain embodiments, the population includes water-dispersible semiconductor nanocrystals and exhibits a quantum yield of greater than about 70%. In certain embodiments, the population includes water-dispersible semiconductor nanocrystals and exhibits a quantum yield of greater than about 75%. In certain embodiments, the population includes water-dispersible semiconductor nanocrystals and exhibits a quantum yield of greater than about 80%. Nanocrystal populations with such high quantum yields can emit light over a broad spectral range. For example, in certain embodiments, the population can exhibit an emission wavelength maximum ranging from about 550 nm to about 850 nm; or about 550 nm to about 650 nm; or about 650 nm to about 750 nm; or about 750 nm to about 850 nm. In specific embodiments, the population includes water-dispersible semiconductor nanocrystals, wherein each nanocrystal includes two different types of oxoacid ligands (e.g., phosphonic acids), exhibits a quantum yield of greater than about 70%, and has an emission wavelength maximum ranging from about 550 nm to about 850 nm.

The at least one of the at least two different oxoacid compounds can be disposed on the semiconductor shell. In certain embodiments, each nanocrystal in the population further includes a hydrophilic overcoating on the external semiconductor shell layer that renders the nanocrystal dispersible in an aqueous medium. In some embodiments, the hydrophilic overcoating surrounds the ligand-coated semiconductor core-shell nanocrystal. In certain embodiments, each nanocrystal in the population can be associated with a biological molecule, cell, or drug.

In yet another aspect, provided herein is a dispersion of semiconductor nanocrystals, including: a population of semiconductor nanocrystals, as described herein; and an aqueous or organic medium (e.g., hexane, decane, toluene, chloroform or a polymer).

In yet another aspect, a kit for labeling cells is provided that includes: a population of semiconductor nanocrystals as described herein; and instructions for labeling cells with the population of nanocrystals.

In yet another aspect, provided herein is a method of identifying a sample or detecting a target species (e.g., cell, cellular component, tissue, or biological molecule) in a sample. The method can include: contacting a sample suspected of containing a target species with a population of semiconductor nanocrystals as disclosed herein for a time sufficient to bind the target species to at least one nanocrystal in the population; and monitoring fluorescence emission to detect the presence of the at least one nanocrystal, thereby detecting the target species in the sample. The fluorescence emission can be detected, for example, by imaging (e.g., using a fluorescence microscope) or using a flow cytometer.

In yet another aspect, a method of imaging a cell, cellular component or tissue is provided. The method can include: contacting the cell, cellular component or tissue with a population of semiconductor nanocrystals for a time sufficient to label the cell, cellular component or tissue with the nanocrystals; and detecting the fluorescence emission of the nanocrystals.

In yet another aspect, provided herein is the use of any one of nanocrystals or compositions described herein, which includes contacting a population of semiconductor nanocrystals with a cell, cellular component, tissue, or biological molecule.

In yet another aspect, provided herein is a method for measuring the amount of an organic ligand (e.g., oxoacid) on a semiconductor nanocrystal, comprising:

separating the organic ligand from the surface of a semiconductor nanocrystal to provide a sample that includes the organic ligand; and analyzing the sample spectroscopically to measure the amount of the organic ligand in the sample.

DETAILED DESCRIPTION

Figure 1:
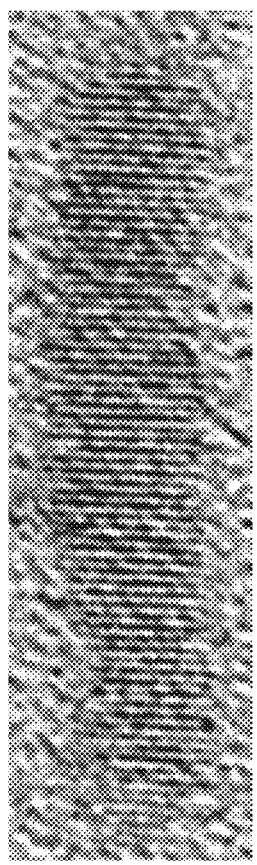
FIG. 1 is TEM micrograph of an elongated semiconductor nanocrystal showing x, y, and z-axis orientation.
Figure 1:
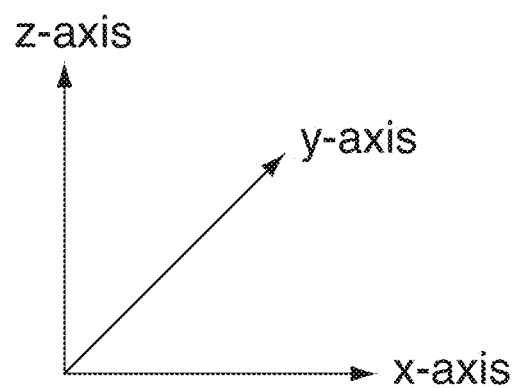

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "about", when used to describe a numerical value, shall encompass a range up to ±15% of that numerical value, unless the context clearly dictates otherwise.

While compositions and methods are described in terms of "comprising" various components or steps (interpreted as meaning "including, but not limited to"), the compositions and methods can also "consist essentially of" or "consist of" the various components and steps, such terminology should be interpreted as defining essentially closed-member groups.

"Nanocrystal" as used herein can refer to a nanoparticle made out of an inorganic substance that typically has an ordered crystalline structure. It can refer to a nanocrystal having a crystalline core (core nanocrystal), or to a core/shell nanocrystal. Typically, a nanocrystal has a core diameter ranging from 1-100 nm in its largest dimension.

"Core nanocrystal" refers to a nanocrystal to which no inorganic shell has been applied; typically it is a semiconductor nanocrystal, and typically it is made of a single semiconductor material. It can have a homogeneous composition, or its composition can vary with depth inside the nanocrystal. Many types of nanocrystals are known, and any suitable method for making a nanocrystal core and applying a shell to the core may be employed.

"Semiconductor nanocrystal" or "quantum dot" as used herein refers to a nanocrystalline particle made from a material that in the bulk is a semiconductor or insulating material, which has a tunable photophysical property in the near ultraviolet (UV) to far infrared (IR) range.

"Water-soluble" or "water-dispersible" is used herein to mean the item can be soluble or suspendable in an aqueous-based solution, such as in water or water-based solutions or buffer solutions, including those used in biological or molecular detection systems as known by those skilled in the art. While water-soluble nanoparticles are not truly 'dissolved' in the sense that term is used to describe individually solvated small molecules, they are solvated (via hydrogen, electrostatic or other suitable physical/chemical bonding) and suspended in solvents that are compatible with their outer surface layer, thus a nanoparticle that is readily dispersed in water is considered water-soluble or water-dispersible. A water-soluble nanoparticle can also be considered hydrophilic, since its surface is compatible with water and with water solubility.

Also provided herein are novel semiconductor nanocrystal compositions and methods for preparing these compositions. Stable populations of nanocrystals are provided that exhibit high (>50%) quantum yield in both organic and aqueous solution. The composition can be a dispersion of nanocrystals. For example, dispersions can include a population of nanocrystals as described herein; and an aqueous or organic medium. The organic medium can include an organic solvent or a polymer. The aqueous medium can include water, buffer, saline, or any type of biologically compatible fluid. Because the nanocrystals provided herein do not dim significantly when dispersed in an aqueous medium (e.g., deionized water, borate buffer, carbonate buffer, or phosphate buffer), even at low concentrations or upon prolonged exposure to aqueous solvents, these nanocrystals also can be used in various biological applications. Nanocrystals provided herein also can be used in non-biological applications. For example, nanocrystals, as provided herein, can be included as a component in a photovoltaic or light-emitting (e.g., electroluminescent) device such as a light emitting diodes (LEDs) and solar panels. In one embodiment, nanocrystals are suspended in a medium (e.g., aqueous or non-aqueous carrier) and can be used as a fluorescent ink.

In general, the provided methods utilize a mixture of at least two different organic ligands during nanocrystal synthesis. Organic ligands are compounds capable of binding (e.g., coordinating) to the semiconductor precursors and/or atoms residing on the nanocrystal surface. The ligand mixtures described herein can be used in the manufacture of the semiconductor core and/or the semiconductor shell. The methods are particularly applicable to the synthesis of semiconductor shells where organic ligands (e.g., amines, alcohols, ethers, alkenes, and alkynes) are used in the shell growth reaction.

In certain embodiments, methods are provided herein that include contacting a semiconductor core with semiconductor shell precursor(s) and heating the mixture in the presence of two or more organic ligands. Various types of organic ligands can be used in the disclosed methods and are described herein, including, for example, organic ligands that include one or more acidic groups or derivatives thereof (e.g., conjugate bases, salts or esters) capable of coordinating with semiconductor precursors and/or atoms on the nanocrystal surface.

In certain embodiments, the two or more organic ligands (e.g., acidic ligands or conjugate bases thereof) are used in the manufacture of the semiconductor shell. A representative method includes combining a plurality of semiconductor nanocrystal cores, at least one solvent, a first semiconductor shell precursor, and a second semiconductor shell precursor, wherein the first and second semiconductor shell precursors are different, and at least two different acidic compounds to provide a reaction mixture. The reaction mixture is heated for a period of time sufficient to induce formation of a semiconductor shell layer on at least one core. The components of the reaction mixture can be added in any order. In one representative method, the plurality of semiconductor nanocrystal cores can be combined with the at least one solvent and the at least two different organic (e.g., acidic) compounds to provide a reaction mixture. The first and second semiconductor shell precursors are then added to this reaction mixture. In another representative method, the plurality of semiconductor nanocrystal cores are first combined with the at least one solvent. The first and second semiconductor shell precursors and the at least two different oxoacid compounds then are added.

Purified or non-purified cores can be utilized in the production methods described herein. In certain methods, the plurality of purified semiconductor nanocrystal cores can be combined with at least one solvent and at least two different organic compounds to provide a reaction mixture. Alternatively, nanocrystal cores can be used directly after synthesis and without further purification. In certain methods, where a mixture of organic (e.g., oxoacid) ligands is used in the core synthesis, unreacted organic ligands can be present in sufficient quantities, such that it may not be necessary to supply additional organic (e.g., oxoacid) ligands in the reaction mixture. Thus, provided herein is a method that includes providing a reaction mixture that includes a plurality of semiconductor nanocrystal cores, at least two different acidic compounds, and at least one solvent. A first semiconductor shell precursor and a second semiconductor shell precursor, wherein the first and second semiconductor shell precursors are different, then are added to the reaction mixture and heated for a period of time sufficient to induce formation of a semiconductor shell layer on at least one core.

In certain methods, additional shell precursor s having compositions different than the first and second shell precursors can be used in the synthetic methods described herein, For example, three or more shell precursors can added to the reaction mixture to form the semiconductor shell on the semiconductor core. Alternatively, mixtures of precursors can be combined prior to addition into the reaction mixture. For example, a first shell precursor (e.g., cadmium or selenium precursor) can be used in conjunction with second and third shell precursors (e.g., zinc and sulfur precursors) to form a CdZnS or ZnSeS shell.

In certain aspects, nanocrystal shells can be synthesized to the desired size by sequential, controlled addition of two or more semiconductor materials to build and/or apply monolayers of shell material to the core. This synthetic approach differs from conventional methods of adding shells where materials (e.g., diethylzinc and bis(trimethylsilyl)sulfide) are added concurrently during the synthesis. Further, sequential addition permits the formation of relatively thick (e.g., >2 nm), uniform shells (e.g., uniform size and depth) on a core. Appropriate amounts of the shell precursors are added to form a single monolayer to each nanocrystal core. The amount of shell precursors that need to be added for each monolayer addition is based on the starting size of the underlying core. Since the underlying core size typically increases over the course of the reaction, a new "core" size needs to be determined with each addition by taking the previous "core" volume and adding to it the thickness of just-added shell monolayer.

Each monolayer of shell material can be independently selected, and may be made up of a single component, or may comprise a multi-component (e.g., alloyed) shell material. In some embodiments, it is suitable to apply one or more sequential monolayers of a first shell material, followed by one or more sequential monolayers of a second shell material. Nanocrystals prepared using layer additions of shell precursors allows the deposition of at least one inner shell layer of a material having a bandgap and lattice size compatible with the core, followed by the deposition of at least one outer shell layer of a material having a bandgap and lattice size compatible with the inner shell layer. In some embodiments, multiple sequential monolayers of a single shell material can be applied to provide a uniform shell of a desired number of monolayers of a single shell material; in these embodiments, the first and second shell materials are the same. In other embodiments, sequential monolayers of an alloyed shell material are applied, where the ratio of the components varies such that the composition becomes successively enriched in one component of the multi-component mixture as the successive monolayers of shell material are deposited.

Certain methods provided herein can be used to prepare nanocrystals or populations thereof that include a semiconductor core and an alloyed shell. Nanocrystals including alloyed shells of the requisite thickness can be produced using any number of procedures. Certain methods provided herein allow for fine and controlled addition of semiconductor shell precursors to induce self-assembly of an alloy during the shell growth reaction. A "self-assembled alloy," as used herein, refers to an alloy, such as an alloy of semiconductor materials, in which the components spontaneously assemble until a stable, ordered structure of minimum energy is reached. Self-assembled alloys can be formed when two or more semiconductor precursors having similar reactivity are simultaneously present in a nanocrystal growth solution (e.g., a solution containing a plurality of nanocrystal cores). Semiconductor precursors typically find their appropriate location, e.g., by diffusing through a solution, based on their physical and chemical properties. Generally, a self-assembled alloy can be formed when the semiconductor precursor(s) is added to the solution in excess relative to the amount of nanocrystals. One method for preparing a self-assembled alloy involves applying sequential monolayers of shell material to the nanocrystal cores, where the ratio of the semiconductor precursors is varied over the course of monolayer deposition. As the successive monolayers of shell material are deposited, the shell composition becomes successively enriched in one component. Once the desired number of monolayers has been deposited, the shell precursors can self-assemble to form an alloy. Since the precursor(s) are used in excess relative to the growing nanocrystals, these precursors remain unreacted in the reaction mixture upon addition of further precursor materials. This is in contrast to methods wherein a stoichiometric or near-stoichiometric amount of semiconductor precursors are added to a reaction mixture containing nanocrystals and fully or nearly-fully reacted prior to adding further precursor materials.

Thus, in one method, successive additions of a solution of shell precursors (e.g., cadmium, sulfur and zinc precursors) are added to semiconductor cores (e.g., CdSe) to form a relatively thick, homogeneous alloyed shell on the cores. In another method, constant concentrations of different shell precursors are added to a solution of cores in an alternating manner. For example, solutions of shell precursors can be added one at a time in an alternating manner and then allowed to react (i.e., self-assemble) for a given time period to form an alloyed shell. In yet another method, a first solution of shell precursor (e.g., cadmium precursor) can be added to a solution of cores in an alternating manner with a solution containing a second shell precursor or a mixture of two or more shell precursors (e.g., sulfur and zinc precursors). Upon addition of the first and second precursor solutions, an alloyed shell can self-assemble on the nanocrystal. Successive, alternating layer additions of shell precursors can be applied to the nanocrystal to build up the desired thickness of shell material.

Also provided herein is a method of producing semiconductor nanocrystal cores. A representative method for producing nanocrystal cores includes combining in any suitable order a first semiconductor precursor, a second semiconductor precursor, at least one coordinating solvent, and at least two different organic ligands to form a reaction mixture. The reaction mixture is heated to a temperature that is sufficiently high to form nanocrystal cores and can be stopped by cooling to halt nanocrystal growth.

Various types of organic ligands can be used in the practice of the methods described herein. For example, certain methods utilize a mixture of acidic compounds. The disclosed methods are not limited to the type of acid and can be generalized to include mixtures of acids and more complex mixtures of more than two acids (as well as derivatives thereof).

Oxoacids are one suitable class of acidic compounds that can be used in the methods described herein. An "oxoacid" (also sometimes referred to as an "oxyacid," "oxo acid," "oxy-acid," "oxiacid," or "oxacid") refers to an acid that includes oxygen, at least one element other than oxygen, at least one hydrogen atom bound to oxygen, and forms an ion upon loss of one or more protons. The term stands in contradistinction to "hydracids," which lack oxygen, such as, e.g., hydrochloric acid (HCl) or hydrofluoric acid (HF). Examples of oxoacids include carboxylic acids, sulfuric acid, nitric acid, phosphoric acid, and halogen-containing oxoacids, such as hypochlorous acid, chlorous acid, chloric acid, perchloric acid, perbromic acid and metaperiodic acid. Exemplary oxoacids can include hydrons (i.e., a positive hydrogen cation, $H^+$), for example, $P(OH)_3$, $RC(=O)OH$, $HOSOH$, $HOCl$, $HON=O$, $(HO)_2SO_2$, $RP(=O)(OH)_2$. Certain types of oxoacids can produce a conjugate base by loss of positive hydrogen ion(s). As used herein, the term "oxoacid" or "oxoacid compound" also encompasses an oxoacid derivative. Thus, in certain methods provided herein, one or more of the oxoacid compounds used in such methods can be in the form of an oxoacid derivative. Oxoacids and derivatives thereof (e.g., conjugate bases, salts or esters) can be added to the reaction mixture directly or can be formed during the course of the reaction process.

Exemplary oxoacid derivatives include, for example, conjugate bases, salts, and esters (e.g., diesters, triesters, and the like) of oxoacids. In certain embodiments, oxoacid can be in the form of a conjugate base or salt. Representative examples of such derivatives include, without limitation, n-alkyl cadmium phosphonate, n-alkyl zinc phosphonate, n-alkyl cadmium carboxylate, n-alkyl zinc carboxylate and the like. In some embodiments, the n-alkyl portion of the phosphonate can be any hydrocarbon compound (e.g., alkanes, alkenes, and alkynes of which any can be linear, branched, or cyclic). In certain embodiments, oxoacid compounds can be in the form or an ester. Oxoacid esters typically include at least one hydroxyl group that has been replaced by an alkyl (alkoxy) group. Oxoacid esters can be generated, for example, by reacting an oxoacid with a hydroxyl compound (e.g., an alcohol or phenol). Representative oxoacid esters that can be used in the practice of the disclosed methods include, for example and without limitation, di-n-alkyl n-alkylphosphonate, mono-n-alkyl n-alkylphosphonate, and the like.

"Alkyl" or "alkyl group" as used herein typically refers to a branched or unbranched saturated hydrocarbon group of 1 to 100 carbon atoms, preferably 1 to 30 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. Optionally, an alkyl can contain 1 to 6 linkages selected from the group consisting of —O—, —S—, -M- and —NR— where R is hydrogen, or $C_1$-$C_8$ alkyl or lower alkenyl. In addition to the alkyl groups identified herein, other possible alkyl groups can be used in the practice of the described methods.

The methods provided herein implement a mixture of at least two oxoacid compounds. Typically, a mixture of two oxoacid compounds is utilized. The oxoacid compounds can differ with respect to composition and/or molecular weight. In certain embodiments, the two or more oxoacid compounds have a similar acidic head group but differ in molecular weight. Suitable oxoacids for use in the disclosed methods include a phosphonic acid head group. Conjugate bases, salts or esters (e.g., diesters) of phosphonic acids can be used in certain methods. Exemplary phosphonic acid compounds include alkylphosphonic acid compounds, such as, for example, $C_1$-$C_{20}$ alkylphosphonic acid compounds, where the alkyl group can be linear or branched (e.g., tetradecylphosphonic acid, methylphosphonic acid, ethylphosphonic acid, butylphosphonic acid, hexylphosphonic acid, octylphosphonic acid, and the like).

Particular methods utilize a mixture of two different phosphonic acid compounds. In certain embodiments, a mixture of two alkylphosphonic acid compounds can be used to prepare the nanocrystal shell. For example, a first phosphonic acid compound can be selected from $C_1$-$C_{10}$ alkylphosphonic acid compounds and a second phosphonic acid compound can be selected from $C_{10}$-$C_{20}$ alkylphosphonic acid compounds. In certain methods, a mixture a $C_{10}$-$C_{20}$ alkylphosphonic acid compound (e.g., TDPA) and at least one $C_1$-$C_{10}$ alkylphosphonic acid compound, such as ethylphosphonic acid (EPA) can be used. In other methods, a mixture of a $C_{10}$-$C_{20}$ alkylphosphonic acid compound (e.g., TDPA) and at least one $C_1$-$C_{10}$ alkylphosphonic acid compound, such as methylphosphonic acid, butylphosphonic acid, hexylphosphonic acid, or octylphosphonic acid can be used.

Other suitable oxoacids for use in the disclosed methods can include a carboxylic acid head group. Conjugate bases of carboxylic acids can be used in certain methods. Suitable carboxylic acids include $C_1$-$C_{20}$ carboxylic acids, where the alkyl group can be linear or branched (e.g., lauric acid, myristic acid, palmitic acid, and stearic acid, acetic acid, propionic acid, butyric acid, hexanoic acid, and octanoic acid). In some embodiments, a mixture of at least one $C_{10}$-$C_{20}$ carboxylic acid and at least one $C_1$-$C_{10}$ carboxylic acid can be used. In certain embodiments, a mixture of two alkyl carboxylic acid compounds is used to prepare the nanocrystal shell. For example, a first alkyl carboxylic acid compound can be selected from $C_1$-$C_{10}$ alkylcarboxylic acid compounds and a second carboxylic acid compound can be selected from $C_{10}$-$C_{20}$ alkylcarboxylic acid compounds Other types of oxoacids that can be used in the practice of the methods provided herein include sulfonic acids and boronic acids and conjugates bases and mixtures thereof. A sulfonic acid or boronic acid also can be used in combination with a phosphonic acid and/or a carboxylic acid compound, as described herein.

Particular methods utilize a mixture of two or more phosphonic acid compounds, or a mixture of two or more carboxylic acid compounds, or a mixture of two or more boronic acid compounds, or a mixture of two or more sulfonic acid compounds, or a mixture of two or more deprotonated conjugate bases of any of these acidic compounds (e.g., carboxylate compounds) or a mixture of any of these acidic compounds. Certain methods utilize a mixture of at least two different carboxylic acid compounds. Certain methods utilize a mixture of at least one phosphonic acid or conjugate base thereof and at least one carboxylic acid or a deprotonated conjugate base thereof.

In certain embodiments, the mixture of organic ligands can include a lower molecular weight acidic ligand and a higher molecular weight acidic ligand. Thus, in one aspect, the method provides a reaction mixture that includes a plurality of semiconductor nanocrystal cores, at least one solvent, a first and second semiconductor shell precursors, a first acidic compound and a second acidic compound, wherein the first and second acidic compounds have two different molecular weights. In certain embodiments, the lower molecular weight compound has a MW of about 50 grams per mole (g/mol) to about 200 g/mol, and the higher molecular weight compounds has a MW of about 200 g/mol to about 300 g/mol. Certain embodiments utilize a lower molecular weight compound with a MW of about 100 g/mol to about 120 g/mol and a higher molecular weight compound with a MW of about 250 to about 300 g/mol. Certain embodiments utilize a lower molecular weight compound with a MW of about 110 g/mol to about 115 g/mol and a higher molecular weight compound with a MW of about 275 g/mol to about 280 g/mol.

The relative amounts of the two or more acidic compounds can be tailored to optimize the physical and optical properties of the nanocrystal. For example, increasing the amount of the lower molecular weight ligand used in the shell reaction mixture can enhance the quantum yield of the nanocrystal as compared to when only a single acidic compound is used in the reaction. The increase in quantum yield has been demonstrated in both aqueous and organic solution.

The relative amounts of lower and higher molecular weight acidic compounds also can alter the emission wavelength of the resulting particle. For example, an increase in the amount of a lower molecular weight acidic compound (e.g., EPA) relative to higher molecular weight acidic compound (e.g., TDPA) can cause a corresponding shift of the emission wavelength to longer wavelengths (i.e., red-shifting). For example, a shift of about 5 nm to about 15 nm can be achieved by adjusting the ratio of EPA to TDPA used in the shelling reaction mixture. This effect can depend on the size and/or shape of the nanocrystal core. For certain types of nanocrystals (e.g., rod-shaped), red-shifting of emission wavelength is thought to occur as a result of differential deposition of shell material along the longitudinal (z) and lateral (x and y) axes of the particle, where FIG. 1 illustrates the x, y, and z dimensions of a non-spherical nanocrystal. Surprisingly, for an elongated nanocrystal, the use of a mixture of acidic compounds according to the disclosed methods favors deposition of shell material along the shorter axes (x and y axis). In certain methods, as shell is deposited along the x and y axis of an elongated particle, the particle becomes less elongated (i.e., more spherical), and the emission peak shifts to a longer wavelength While not wishing to be bound by theory, it is thought that as such a particle becomes more spherical, quantum confinement is reduced, resulting in a red-shift in the particle's emission wavelength.

In certain methods, the deposition of shell material along the x and y axis of the nanocrystal core can be controlled by adjusting the ratio of organic compounds and/or the shape of the core nanocrystal, used in the reaction mixture. The ratios of the two different organic compounds can be altered depending on the type of materials used and the properties desired.

The ratio of two different compounds in a mixture can be expressed in terms of a mole fraction. The "mole fraction," as used herein refers to the ratio of the number of moles of one constituent of a mixture or solution to the total number of moles of all the constituents. By way of example, in the case where a mixture of two compounds is used in a reaction mixture, the mole fraction of one of the two compounds in the mixture can be expressed according to the following equation:

$$\text{Mole Fraction of Compound \#1} = \frac{(\text{\# moles of Compound \#1})}{(\text{\# moles of Compound \#1} + \text{\# moles of Compound \#2})}$$

When the mixture includes a lower molecular weight organic ligand and a higher molecular weight organic ligand, the mole fraction of lower molecular weight ligand in the mixture can range from about 0.1% to about 99.9%; or about 0.1% or greater; or about 0.5% or greater; or about 1% or greater; or about 2% or greater; or about 5% or greater; or about 10% or greater; or about 15% or greater; or about 20% or greater; or about 50% or greater; or about 75% or greater. Conversely, the mole fraction of higher molecular weight ligand can range from about 0.1% to about 99.9%; or about 0.1% or greater; or about 0.5% or greater; or about 1% or greater; or about 2% or greater; or about 5% or greater; or about 10% or greater; or about 15% or greater; or about 20% or greater; or about 50% or greater; or about 75% or greater. In certain embodiments, the mole fraction of lower molecular weight ligand (or higher molecular weight ligand) is less than 50%. In some embodiments, the mole fraction of the lower molecular weight ligand (or higher molecular weight ligand) can be about 1% to about 10%; or about 1% to about 15%; or about 1% to about 20%. In some embodiments, the mole fraction of the lower molecular weight ligand (or higher molecular weight ligand) can be about 0.1% to about 10%; or about 0.1% to about 15%; or about 0.1% to about 20%. In some embodiments, the lower molecular weight compound is an acidic ligand, In other embodiments, the lower molecular weight compound is an oxoacid. In yet other embodiments, the lower molecular weight compound is a phophonic acid.

In certain embodiments, the reaction mixture can include two phosphonic acid compounds having two different molecular weights, wherein the mole fraction of the lower molecular weight phosphonic acid is greater than about 0.1%; or greater than about 1%; or greater than about 2%; or greater than about 3%; or greater than about 4%; or greater than about 5%; or greater than about 10%; or greater than about 20%. In some embodiments, the mole fraction of the lower molecular weight phosphonic acid is about 0.1% to about 20%; or about 1% to about 20%; or about 2% to about 20%; or about 3% to about 20%; or about 4% to about 20%; or about 5% to about 20%. Reaction mixtures containing oxoacid ligands in the amounts described above can be used to produce either nanocrystal shells or nanocrystal cores.

The methods provided herein are applicable to the manufacture of various types of nanocrystals. Such nanocrystals can include Group 2-16, 12-16, 13-15 and 14 element-based semiconductors such as ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlAs, AlP, AlSb, PbS, PbSe, Ge and Si or a mixture thereof.

The nanoparticles described herein typically include a shell material that has a higher bandgap than the core material. However, other arrangements are also possible. Typically, the core and the shell of a core/shell nanocrystal are composed of different semiconductor materials, meaning that at least one atom type of a semiconductor material of the core of a core/shell nanocrystal is different from the atom types in the shell of the nanocrystal. In certain embodiments, the core includes a Group II-VI, Group II-VI-VI, Group III-V, Group III-III-V, Group III-V-V or a Group semiconductor material. For example, the core can include a Group II-VI semiconductor material, such as, CdS, CdSe, CdTe, ZnS, ZnSe, ZnTe, HgS, or a mixture thereof. For such materials, the shell layer can include a Group II-VI, a Group II-VI-VI, Group III-V, Group III-III-V, Group III-V-V or a Group semiconductor material. For example, the shell can include a Group II-VI semiconductor material, such as BeO, BeS, BeSe, MgO, MgS, MgSe, ZnO, ZnS, ZnSe, CdO, CdS or a mixture thereof. In certain embodiments, both the core and the shell are formed of a Group II-VI semiconductor material. For example, the core can include CdSe, CdTe, or a mixture thereof, and the shell can include ZnS, CdS, or a mixture thereof.

In addition to having a bandgap energy greater than the semiconductor nanocrystal core, suitable materials for the shell can have good conduction and valence band offset with respect to the core semiconductor nanocrystal. Thus, the conduction band is desirably higher and the valence band is desirably lower than those of the core semiconductor nanocrystal. For semiconductor nanocrystal cores that emit energy in the visible (e.g., CdS, CdSe, CdTe, ZnS, ZnSe, ZnTe, GaP, GaAs, GaN) or near IR (e.g., InP, InAs, InSb, PbS, PbSe), a material that has a bandgap energy in the ultraviolet regions may be used. Exemplary materials include CdS, CdSe, InP, InAs, ZnS, ZnSe, ZnTe, GaP, GaN, and magnesium chalcogenides, e.g., MgS, MgSe, and MgTe. For a semiconductor nanocrystal core that emits in the near IR, materials having a bandgap energy in the visible, such as CdS or CdSe, may also be used. It is also understood in the art that the actual fluorescence wavelength for a particular nanocrystal core depends upon the size of the core as well as its composition, so the categorizations above are approximations, and nanocrystal cores described as emitting in the visible or the near IR can actually emit at longer or shorter wavelengths depending upon the size of the core.

In some embodiments, the metal atoms of a shell layer are selected from Cd, Zn, Ga and Mg. The second element in these semiconductor shell layers is frequently selected from S, Se, Te, P, As, N and Sb.

The disclosed methods can use one or more shell precursor compounds. In certain embodiments, a shell is prepared using two or more shell precursor compounds.

Precursors useful as the "first" precursor in the methods provided herein include compounds containing elements from Groups 2 and 12 of the Periodic Table of the Elements (e.g., Zn, Cd, Hg, Mg, Ca, Sr, Ba, and the like), compounds containing elements from Group 13 of the Periodic Table of the Elements (Al, Ga, In, and the like), and compounds containing elements from Group 14 of the Periodic Table of the Elements (Si, Ge, Pb, and the like). Many forms of the precursors can be used in the disclosed methods.

Examples of compounds useful as the first precursor can include, but are not limited to: organometallic compounds such as alkyl metal species, salts such as metal halides, metal acetates, metal carboxylates, metal phosphonates, metal phosphinates, metal oxides, or other salts. In some embodiments, the first precursor provides a neutral species in solution. For example, alkyl metal species such as diethylzinc ($Et_2Zn$) or dimethyl cadmium are typically considered to be a source of neutral zinc atoms ($Zn^0$) in solution. In other embodiments, the first precursor provides an ionic species (i.e., a metal cation) in solution. For example, zinc chloride ($ZnCl_2$) and other zinc halides, zinc acetate ($Zn(OAc)_2$) and zinc carboxylates are typically considered to be sources of $Zn^{2+}$ cations in solution.

By way of example only, suitable first precursors providing neutral metal species include dialkyl metal sources, such as dimethyl cadmium ($Me_2Cd$), diethyl zinc ($Et_2Zn$), and the like. Suitable first precursors providing metal cations in solution include, e.g., cadmium salts, such as cadmium acetate ($Cd(OAc)_2$), cadmium nitrate ($Cd(NO_3)_2$), cadmium oxide (CdO), and other cadmium salts; and zinc salts such as zinc chloride ($ZnCl_2$), zinc acetate ($Zn(OAc)_2$), zinc oleate ($Zn(oleate)_2$), zinc chloro(oleate), zinc undecylenate, zinc salicylate, and other zinc salts. In some embodiments, the first precursor is salt of Cd or Zn. In some embodiments, the first precursor is a halide, acetate, carboxylate, or oxide salt of Cd or Zn. In other embodiments, the first precursor is a salt of the form $M(O_2CR)X$, wherein M is Cd or Zn; X is a halide or $O_2CR$; and R is a $C_4$-$C_{24}$ alkyl group that is optionally unsaturated. Other suitable forms of Groups 2, 12, 13 and 14 elements useful as first precursors are known in the art.

Precursors useful as the "second" precursor in the disclosed methods include compounds containing elements from Group 16 of the Periodic Table of the Elements (e.g., S, Se, Te, and the like), compounds containing elements from Group 15 of the Periodic Table of the Elements (N, P, As, Sb, and the like), and compounds containing elements from Group 14 of the Periodic Table of the Elements (Ge, Si, and the like). Many forms of the precursors can be used in the disclosed methods. It will be understood that in some embodiments, the second precursor will provide a neutral species in solution, while in other embodiments the second precursor will provide an ionic species in solution.

In certain embodiments, the first semiconductor shell precursors include Group 2, 12, 13 and 14 element-containing compounds. In certain embodiments, the second semiconductor shell precursors Group 2, 12, 13, 14, 15 and 16 element-containing compounds.

In certain methods, additional shell precursors can be used in the shelling reaction mixture. Any of the first and second shell precursors disclosed herein can be used in such methods. In certain methods, three or more shell precursors are used to prepare the semiconductor shell.

When the first precursor includes a metal cation, the second precursor can provide an uncharged (i.e., neutral) non-metal atom in solution. For example, when the first precursor includes a metal cation, the second precursor contributes a neutral chalcogen atom, most commonly $S^0$, $Se^0$ or $Te^0$.

Suitable second precursors for providing a neutral chalcogen atom include, for example, elemental sulfur (often as a solution in an amine, e.g., decylamine, oleylamine, or dioctylamine, or an alkene, such as octadecene), and trialkylphosphine adducts of S, Se and Te. Such trialkylphosphine adducts are sometimes described herein as $R_3P=X$, wherein X is S, Se or Te, and each R is independently H, or a $C_1$-$C_{24}$ hydrocarbon group that can be straight-chain, branched, cyclic, or a combination of these, and which can be unsaturated. Exemplary second precursors of this type include tri-n (butylphosphine)selenide (TBP=Se), tri-n-(octylphosphine)selenide (TOP=Se), and the corresponding sulfur and tellurium reagents, TBP=S, TOP=S, TBP=Te and TOP=Te. These reagents are frequently formed by combining a desired element, such as Se, S, or Te with an appropriate coordinating solvent, e.g., TOP or TBP. Precursors that provide anionic species under the reaction conditions are typically used with a first precursor that provides a neutral metal atom, such as alkylmetal compounds and others described above or known in the art.

In some embodiments, the second precursor provides a negatively charged non-metal ion in solution (e.g., S-2, Se-2 or Te-2). Examples of suitable second precursors providing an ionic species include silyl compounds such as bis(trimethylsilyl)selenide (($TMS)_2Se$), bis(trimethylsilyl)sulfide (($TMS)_2S$) and bis(trimethylsilyl)telluride (($TMS)_2Te$). Also included are hydrogenated compounds such as $H_2Se$, $H_2S$, $H_2Te$; and metal salts such as NaHSe, NaSH or NaHTe. In this situation, an oxidant can be used to oxidize a neutral metal species to a cationic species that can react with the anionic precursor in a 'matched' reaction, or an oxidant can be used increase the oxidation state of the anionic precursor to provide a neutral species that can undergo a 'matched' reaction with a neutral metal species.

Other exemplary organic precursors are described in U.S. Pat. Nos. 6,207,299 and 6,322,901 to Bawendi et al., and synthesis methods using weak acids as precursor materials are disclosed by Qu et al., (2001), Nano Lett., 1(6):333-337, the disclosures of each of which are incorporated herein by reference in their entirety.

Nanoparticle shell precursors can be represented as an M-source and an X-donor. The M-source can be an M-containing salt, such as a halide, carboxylate, phosphonate, carbonate, hydroxide, or diketonate, or a mixed salt thereof (e.g., a halo carboxylate salt, such as Cd(halo)(oleate)), of a metal, M, in which M can be, e.g., Cd, Zn, Mg, Hg, Al, Ga, In, or Tl. In the X-donor, X can be, e.g., O, S, Se, Te, N, P, As, or Sb. The mixture can include an amine, such as a primary amine (e.g., a $C_8$-$C_{20}$ alkyl amine). The X donor can include, for example, a phosphine chalcogenide, a bis(trialkylsilyl)chalcogenide, a dioxygen species, an ammonium salt, or a tris(trialkylsilyl)phosphine, or the like.

The M-source and the X donor can be combined by contacting a metal, M, or an M-containing salt, and a reducing agent to form an M-containing precursor. The reducing agent can include an alkyl phosphine, a 1,2-diol or an aldehyde, such as a $C_6$-$C_{20}$ alkyl diol or a $C_6$-$C_{20}$ aldehyde.

Suitable M-containing salts include, for example, cadmium acetylacetonate, cadmium iodide, cadmium bromide, cadmium chloride, cadmium hydroxide, cadmium carbonate, cadmium acetate, cadmium oxide, zinc acetylacetonate, zinc iodide, zinc bromide, zinc chloride, zinc hydroxide, zinc carbonate, zinc acetate, zinc oxide, magnesium acetylacetonate, magnesium iodide, magnesium bromide, magnesium chloride, magnesium hydroxide, magnesium carbonate, magnesium acetate, magnesium oxide, mercury acetylacetonate, mercury iodide, mercury bromide, mercury chloride, mercury hydroxide, mercury carbonate, mercury acetate, aluminum acetylacetonate, aluminum iodide, aluminum bromide, aluminum chloride, aluminum hydroxide, aluminum carbonate, aluminum acetate, gallium acetylacetonate, gallium iodide, gallium bromide, gallium chloride, gallium hydroxide, gallium carbonate, gallium acetate, indium acetylacetonate, indium iodide, indium bromide, indium chloride, indium hydroxide, indium carbonate, indium acetate, thallium acetylacetonate, thallium iodide, thallium bromide, thallium chloride, thallium hydroxide, thallium carbonate, or thallium acetate. Suitable M-containing salts also include, for example, carboxylate salts, such as oleate, stearate, myristate, and palmitate salts, mixed halo carboxylate salts, such as M(halo)(oleate) salts, as well as phosphonate salts.

The X donor is a compound capable of reacting with the M-containing salt to form a material with the general formula MX. The X donor is generally a chalcogenide donor or a phosphine donor, such as a phosphine chalcogenide, a bis(silyl) chalcogenide, dioxygen, an ammonium salt, or a tris(trialkylsilyl) phosphine. Suitable X donors include dioxygen, elemental sulfur, bis(trimethylsilyl) selenide (($TMS)_2Se$), trialkyl phosphine selenides such as (tri-n-octylphosphine) selenide (TOPSe) or (tri-n-butylphosphine) selenide (TBPSe), trialkyl phosphine tellurides such as (tri-n-octylphosphine) telluride (TOPTe) or hexapropylphosphorustriamide telluride (HPPTTe), bis(trimethylsilyl) telluride (($TMS)_2Te$), sulfur, bis(trimethylsilyl)sulfide (($TMS)_2S$), a trialkyl phosphine sulfide such as (tri-n-octylphosphine) sulfide (TOPS), tris(dimethylamino) arsine, an ammonium salt such as an ammonium halide (e.g., $NH_4Cl$), tris(trimethylsilyl) phosphide (($TMS)_3P$), tris(trimethylsilyl) arsenide (($TMS)_3As$), or tris(trimethylsilyl) antimonide (($TMS)_3Sb$). In certain embodiments, the M donor and the X donor can be moieties within the same molecule.

In some embodiments, mismatched precursors can be chosen such that one precursor provides a neutral atom in solution under the reaction conditions, while the other precursor provides an ion. For example, a mixture of cadmium alkylphosphonate, which is a source of $Cd^{2+}$ ions, and trioctylphosphine selenide (TOPSe), which is a source of $Se^0$, might be employed as mismatched precursors. Such precursors cannot react to form a neutral species unless an electron transfer agent is present to adjust the oxidation state of one of the reactive species to provide 'matched' species capable of undergoing reaction. For example, a reductant could be used to add electrons to $Cd^{2+}$ to provide two non-ionic species (i.e., $Cd^0$ and $Se^0$), or it could add electrons to $Se^0$ to provide two ionic species (i.e., $Cd^{2+}$ and $Se^{2-}$). Either way, once the atomic species are 'matched', their reaction can proceed, but the reaction cannot proceed without such an electron transfer agent. Alternatively, two ionic species having the same charge (i.e., two cations or two anions) would also be considered to be 'mismatched.' For example, mismatched precursors that provide two cationic species could be used, where one species is reduced to provide an anionic species capable of undergoing a 'matched' reaction. For example, $Se^{2+}$ or $Se^{4+}$ could be reduced to provide selenide anion $Se^{2-}$, which could undergo reaction with a metal cation species, such as $Cd^{2+}$. In another example, two cationic species could both be reduced to neutral species.

The disclosed methods are conducted in a solvent. Various types of solvents can be used. Solvents can be coordinating or non-coordinating solvents. "Coordinating solvent" as used herein refers to a solvent, such as TOP, TOPO, carboxylic acids, and amines, which are effective to coordinate to the surface of a nanocrystal. Coordinating solvents can have heteroatoms that provide bonding pairs of electrons to coordinate with the nanocrystal surface. 'Coordinating solvents' include phosphines, phosphine oxides, phosphonic acids, phosphinic acids, amines, and carboxylic acids, which are often used in growth media for nanocrystals, and which form a coating or layer on the nanocrystal surface. TOP and TOPO are sometimes preferred. Typical coordinating solvents include alkyl amines, alkyl phosphines, alkyl phosphine oxides, alkyl phosphonic acids, alkyl phosphinic acids, or carboxylic acid containing solvents, or mixtures of these.

Coordinating solvents exclude hydrocarbon solvents such as hexanes, toluene, hexadecane, octadecene, and the like, which do not have heteroatoms that provide bonding pairs of electrons to coordinate with the nanocrystal surface. Hydrocarbon solvents that do not contain heteroatoms such as O, S, N or P to coordinate to a nanocrystal surface are referred to herein as "non-coordinating solvents." Representative non-coordinating solvents include, for example, tetradecane, octadecane, octadecene, squalane, squalene.

As used herein, the term 'solvent' refers to a medium that supports, dissolves, or disperses materials and reactions between them, but which does not ordinarily participate in or become modified by the reactions of the reactant materials. However, in certain instances, the solvent can be modified by the reaction conditions. For example, TOP may be oxidized to TOPO, or a carboxylic acid can be reduced to an alcohol.

Suitable reaction solvents include, by way of illustration and not limitation, hydrocarbons, amines, alkyl phosphines, alkyl phosphine oxides, carboxylic acids, ethers, furans, phosphoacids, pyridines and mixtures thereof. The solvent may actually include a mixture of solvents, often referred to in the art as a "solvent system". In some embodiments, the solvent includes at least one coordinating solvent. In certain embodiments, the disclosed methods utilize coordinating solvents, such as, for example, amines, alkyl phosphines, alkyl phosphine oxides, fatty acids, ethers, furans, phosphoacids, pyridines, alkenes, alkynes and combinations thereof. In some embodiments, the solvent system includes a secondary amine and a trialkyl phosphine (e.g., TBP or TOP) or a trialkylphosphine oxide (e.g., TOPO). If the coordinating solvent is not an amine, an amine can be included.

The reaction mixtures can include one or more additional ligands in addition to the mixture of organic (e.g., acidic) ligands described herein. Any ligand compound that can complex with a precursor and/or a nanocrystal can be used. Suitable ligands include, by way of illustration and not limitation, phosphoacids such as hexylphosphonic acid and tetradecylphosphonic acid (TDPA), carboxylic acids such as isomers of octadecanoic acid, amines, amides, alcohols, ethers, alkenes, and alkynes. In some cases, the ligand and the solvent can be the same. In certain embodiments, the semiconductor cores are treated with such an additional ligand prior to conducting the shell growth reaction. For example, the cores can be treated with an amine (e.g., an alkylamine) to prepare them for overcoating with shell precursors. In some embodiments, an amine can be included in the nanocrystal shell reaction mixture.

Technical grade solvents can be used, and benefits can be obtained from the existence of beneficial impurities (e.g., reductants) in such solvents, e.g. TOP, TOPO or both. In certain embodiments, the solvent includes at least one pure coordinating solvent. In certain embodiments, the method utilizes one or more pure organic ligands. Typically, pure solvents or ligands contain less than about 10 volume %, or less than about 5 volume %; and preferably less than about 3 volume % of impurities. Therefore, solvents or ligands (e.g., TOP, TOPO, TDPA, and the like) at greater than about 90%; or greater than about 95%; or greater than about 97% purity are particularly well suited for use in the disclosed methods. In certain embodiments, the solvents or ligands have a purity of about 98%-100%. In certain methods, solvents or ligands have a purity of about 99% or greater. For example, the purity of the oxoacid ligand can be about 99% or greater; or about 99.5%; or about 99.9% or greater. By utilizing pure organic ligands in the disclosed methods, it is possible to precisely control the amount of ligand additive that is spiked into the reaction mixture.

The disclosed shell growth methods can be implemented using nanocrystals having spherical or non-spherical nanocrystal cores. A non-spherical nanocrystal core can have an elongated form (e.g., ellipsoid or rod-shaped), however, other shapes of nanocrystal cores also can be implemented in the practice of the disclosed methods The extent of elongation can be described in terms of an aspect ratio. As aspect ratio defines the ratio of length along the longest axis of the nanocrystal relative to the width along the shortest axis. A spherical nanocrystal has an aspect ratio of 1:1, whereas a non-spherical nanocrystal has an aspect ratio of greater than 1:1 (e.g., 2:1; 3:1; 4:1; 5:1; 6:1 or greater). For example, a non-spherical nanocrystal core can have an aspect ratio of greater than 1:1 but less than about 10:1, or less than about 8:1; or less than about 5:1; or less than about 3:1; or less than about 2:1. In certain embodiments, the nanocrystals core has an aspect ratio of about 1.5:1; or about 2:1; or about 3:1; or about 4:1; or about 5:1; or about 6:1 or about 7:1; or about 8:1; or about 9:1; or about 10:1; or a value between any two of these aspect ratios.

The core-shell nanocrystals produced by the methods described herein can be relatively spherical (i.e., aspect ratio of about 1:1) or can have a non-spherical shape. Non-spherical core-shell nanocrystals can have a symmetrical or an asymmetrical shape. For example, core-shell nanocrystals provided herein can be elongated or rod-shaped. In certain embodiments, core/shell nanocrystals produced by the methods provided herein can have a trigonal or pyramidal form. Thus, in one aspect, non-spherical nanocrystals are provided with an aspect ratio of greater than about 1:1 (e.g., 1.1:1; 1.3:1; 1.5:1; 1.7:1; 2:1; 3:1; 4:1; 5:1; 6:1 or greater). In certain embodiments, core-shell nanocrystals are provided with an aspect ratio of about 1.1:1; or about 1.3:1; or about 1.5:1 or about 2:1; or about 2.5:1; or about 3:1; or an aspect ratio between any two of these values.

Certain methods described herein allow for controlled, differential deposition of shell material along the shorter axes of an elongated nanocrystal, resulting in a less elongated (more spherical) core-shell nanocrystal. Such methods provide the ability to produce a core-shell nanocrystal having a lower aspect ratio than that of the core.

Thus, in another aspect is provided a method for producing a population of semiconductor nanocrystals, comprising: combining a plurality of semiconductor nanocrystal cores, wherein each core has an aspect ratio of greater than 1:1 (e.g., about 2:1 or greater); or about 3:1 or greater; or about 4:1 or greater), at least one solvent, a first semiconductor shell precursor, and a second semiconductor shell precursor, wherein the first and second semiconductor shell precursors are different, and at least two acidic compounds (e.g., oxoacids) to provide a reaction mixture; and heating the reaction mixture for a period of time sufficient to induce formation of a semiconductor shell layer on at least one core, wherein the aspect ratio of the core-shell nanocrystal is less than the aspect ratio of the nanocrystal core (e.g., less than about 4:1; or less than about 3:1; or less than about 2:1; or about 1.1:1 to about 1.9:1).

The methods described herein generate a population of semiconductor nanocrystals. A population of semiconductor nanocrystals includes a plurality of nanocrystals having similar physical and/or optical properties. A typical population of semiconductor nanocrystals includes a semiconductor core and an external semiconductor shell layer disposed on the surface of the semiconductor core. Generally, the semiconductor shell layer surrounds the core in a substantially concentric fashion to full cover the surface of the core.

The nanocrystal(s) can have any diameter, where the diameter is measured along the shortest axis of the nanocrystal. For example, the diameter of the nanoparticle may be from about 1 to about 15 nm, from about 1 nm to about 10 nm, or 1 nm to about 5 nm in its smallest dimension. In some such embodiments, the nanoparticles may have a smallest dimension of about 0.5 nm, about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 25 nm, about 30 nm, about 35 nm, about 40 nm, about 45 nm, about 50 nm and ranges between any two of these values. Also provided herein are populations of nanocrystals where greater than 90% of the nanocrystals in the population have substantially identical diameters. In such embodiments, greater than 90% of the nanocrystals can have a diameter of about 20 nm or less. In other embodiments, greater than 90% of the nanocrystals can have a diameter of about 15 nm or less. In other embodiments, greater than 90% of the nanocrystals can have a diameter of about 10 nm or less.

The color (emitted light) of the nanocrystals provided herein can be "tuned" by varying the size and composition of the particle. Nanocrystals as disclosed herein can absorb a wide spectrum of wavelengths, and emit a relatively narrow wavelength of light. The excitation and emission wavelengths are typically different, and non-overlapping. Depending on the size of the core, these nanocrystal(s) can emit in the UV, visible or IR portions of the electromagnetic spectrum. In certain embodiments, nanocrystals are provided that emit in the UV or visible range of electromagnetic spectrum. In other embodiments, the population emits in the near-IR or IR regions of the spectrum (e.g., greater than about 700 nm). The emission maxima of the disclosed nanocrystal and populations thereof can generally be at any wavelength from about 200 nm to about 1000 nm, and typically about 550 nm to about 850 nm. Examples of emission maxima include about 200 nm, about 400 nm, about 500 nm, about 600 nm, about 700 nm, about 800 nm, or about 1,000 nm and ranges between any two of these values. For example, in certain embodiments, the emission maximum of the population is about 550 nm to about 600 nm. In other embodiments, the emission maximum of the population is about 600 nm to about 650 nm. In other embodiments, the emission maximum of the population is about 650 nm to about 750 nm. In yet other embodiments, the emission maximum of the population is about 750 nm to about 850 nm.

The population of nanocrystals provided herein can be monodisperse (i.e., a small particle size distribution). The nanocrystals of a monodisperse population may be characterized in that they produce a fluorescence emission having a relatively narrow wavelength band. The linewidth can be dictated by the single particle emission linewidth, which can, in turn, depend on the composition of the core material. For example, for certain nanocrystals provided herein, the full width at half maximum (FWHM) can be rather narrow, whereas other types of nanocrystals have much broader linewidths due to the composition of the core material. Generally, the emitted light preferably has a symmetrical emission of wavelengths. Examples of emission widths (FWHM) include less than about 200 nm, less than about 175 nm, less than about 150 nm, less than about 125 nm, less than about 100 nm, less than about 75 nm, less than about 60 nm, less than about 50 nm, less than about 40 nm, less than about 30 nm, less than about 20 nm, and less than about 10 nm. The width of emission is preferably less than about 60 nm full width at half maximum (FWHM), or less than about 50 nm FWHM, and sometimes less than about 40 nm FWHM, less than about 30 nm FWHM or less than about 20 nm FWHM. Depending on the composition of the core material, certain populations of nanocrystals provided herein have a FWHM of less than about 30 nm, whereas other types of nanocrystal populations have much broader linewidths (e.g., about 60 nm to about 80 nm).

The nanocrystal populations provided herein exhibit high quantum yields when measured in organic or aqueous medium. Such high quantum yields are indicative of a population of nanocrystals that are substantially free from crystalline defects that can lead to non-radiative excited state decay or deep trap emission. High quantum yield makes these materials particular useful in many biological and non-biological applications. For example, nanocrystal populations provided herein can exhibit a QY of greater than about 50%; or greater than about 60%; or greater than about 70%; or greater than about 75%; or greater than about 80%; or greater than about 85%; or greater than about 90% or a value between these values when measured in organic or aqueous medium. The superior quality of the core-shell nanocrystals produced by the methods provided herein is evident from the high quantum yields (e.g., greater than about 70%) exhibited by these nanocrystals. The quantum yield of core-shell nanocrystals provided herein generally remains high even after treatment with a water-dispersible coating. Thus, provided herein are water-dispersible, core-shell nanocrystal populations that exhibit a quantum yield of greater than about 70% and emit light over the visible to near-IR spectral range. Also provided herein are water-dispersible, core-shell nanocrystal populations that exhibit a quantum yield of greater than about 70% and a fluorescence emission maximum from about 550 nm to about 650 nm; or about 650 nm to about 750 nm; or about 750 nm to about 850 nm.

In yet another aspect, the methods provided herein can be used to produce bright and efficient, core-shell nanocrystals having high quantum yields (e.g., 50% or greater) across a broad range of excitation wavelengths, when measured in aqueous medium. Certain nanocrystal populations produced according to the methods provided herein exhibit quantum yields of 50% or greater even when excited at relatively high energy (e.g., less than about 540 nm). In certain embodiments, nanocrystal population are provided exhibiting a quantum yield of about 50% or greater when measured at an excitation wavelength of about 480 nm or less In other embodiments, nanocrystal populations are provided exhibiting a quantum yield of about 50% or greater when measured at an excitation wavelength of about 440 nm or less.

The nanocrystals provided herein can include residual amounts of one or more of the at least two different organic ligands used in the reaction mixture. In certain embodiments, the organic ligands can be acidic ligands, as described herein. The acidic ligands can be oxoacid ligands such as, for example, phosphonic acid compounds, carboxylic acid compounds, carboxylate compounds, and mixtures thereof. Certain populations of nanocrystals include residual amounts of at least two different phosphonic acid compounds. For example, the nanocrystal can include a $C_1$-$C_{10}$ alkylphosphonic acid compound (e.g., methylphosphonic acid, ethylphosphonic acid, butylphosphonic acid, hexylphosphonic acid and octylphosphonic acid) and a $C_{10}$-$C_{20}$ alkylphosphonic acid compound (e.g., tetradecylphosphonic acid). In certain embodiments, the nanocrystal includes a residual amount of tetradecylphosphonic acid (TDPA) and ethylphosphonic acid (EPA). In other embodiments, the nanocrystal includes a residual amount of TDPA and methylphosphonic acid, butylphosphonic acid, hexylphosphonic acid, and/or octylphosphonic acid. Other populations of nanocrystals include at least two different carboxylic acid compounds. Yet other populations of nanocrystals include at least one phosphonic acid or a derivative thereof and at least one carboxylic acid or a deprotonated conjugate base thereof.

Residual organic ligands can be disposed on the surface of the semiconductor shell. The amount of each organic ligand on the shell can vary and can depend on various factors, such how tightly the compounds are able to bind to the surface in a chosen solvent system and/or steric effects. Residual organic ligands (e.g., acidic compounds) can be analyzed using various analytical and spectroscopic techniques (e.g., solution- or solid-state NMR spectroscopy or mass spectrometry). Analysis can be conducted directly on the nanocrystal. Alternatively, in certain approaches, it may be desirable to remove the organic ligands from the nanocrystal surface prior to analysis. For example, in one method, organic ligands are separated from the surface of a semiconductor nanocrystal (e.g., by chemically dissociating the ligands) to provide a sample that includes the dissociated organic ligands. The sample then can be analyzed spectroscopically to characterize the type and amount of organic ligand in the sample.

In certain embodiments, the residual amount of ligand(s) on the nanocrystal can include a lower molecular weight and a higher molecular weight compound. The mole fraction of lower molecular weight ligand relative to the higher molecular weight ligand remaining on the nanocrystal can range from about 0.1% to about 99.9%; or about 0.1% or greater; or about 0.5% or greater; or about 1% or greater; or about 2% or greater; or about 5% or greater; or about 10% or greater; or about 15% or greater; or about 20% or greater; or about 50% or greater; or about 75% or greater. Conversely, the mole fraction of higher molecular weight ligand can range from about 0.1% to about 99.9%; or about 0.1% or greater; or about 0.5% or greater; or about 1% or greater; or about 2% or greater; or about 5% or greater; or about 10% or greater; or about 15% or greater; or about 20% or greater; or about 50% or greater; or about 75% or greater. In certain embodiments, the mole fraction of lower molecular weight ligand (or higher molecular weight ligand) is less than 50%. In some embodiments, the mole fraction of the lower molecular weight ligand (or higher molecular weight ligand) can be about 1% to about 10%; or about 1% to about 15%; or about 1% to about 20%. In some embodiments, the mole fraction of the lower molecular weight ligand (or higher molecular weight ligand) can be about 0.1% to about 10%; or about 0.1% to about 15%; or about 0.1% to about 20%. In some embodiments, the lower molecular weight compound is an acidic ligand, In other embodiments, the lower molecular weight compound is an oxoacid In yet other embodiments, the lower molecular weight compound is a phophonic acid.

In certain embodiments, two phosphonic acid compounds having two different molecular weights remain on the surface of the nanocrystal after synthesis, wherein the mole fraction of the lower molecular weight phosphonic acid is greater than about 0.1%; or greater than about 1%; or greater than about 2%; or greater than about 3%; or greater than about 4%; or greater than about 5%; or greater than about 10%; or greater than about 20%. In some embodiments, the mole fraction of the lower molecular weight phosphonic acid is about 0.1% to about 20%; or about 1% to about 20%; or about 2% to about 20%; or about 3% to about 20%; or about 4% to about 20%; or about 5% to about 20%.

The nanocrystals described herein are prepared using organic ligands and are, therefore, dispersible in an organic medium (e.g., hexane, toluene, chloroform, decane and the like). For biological applications, it may be necessary to render the nanocrystals dispersible in an aqueous medium (e.g., water or a buffer). Nanocrystals can be provided with a hydrophilic overcoating on the external semiconductor shell layer that renders the nanocrystal dispersible in an aqueous medium. Numerous approaches have been proposed to render nanoparticles water-dispersible. For example, the nanocrystals can be treated with a surface coating, such as a hydrophilic polymer (e.g., PEG, fatty acids, lipids, amphiphilic polymers, or the like), to improve their solubility in water or to render them water dispersible. For example, nanocrystals can be treated with an amphiphilic polymer, as described in, for example, U.S. Pat. No. 6,649,138 (Adams et al.), which is expressly incorporated herein by reference in its entirety, to provide coated nanocrystals having excellent stability in water. Alternatively, the nanocrystals can be treated with other types of coating materials. In certain methods, a ligand exchange process can be utilized to replace the hydrophobic ligands on the nanoparticles with hydrophilic ligands to cause the plurality of nanocrystals to migrate into the aqueous phase. Typically, such coating materials include a group(s) for attachment to the nanocrystal surface and a hydrophilic group(s), such as carboxylic acids, hydroxyls, amines, and the like. For example, the overcoating can include a ligand that comprises one or more thiol, amine, or phosphonate functional groups. Some examples of small organic ligands include thiol containing compounds (e.g., mercapto caroboxylic acids, such as MUA), bidentate thiols (i.e., DHLA), tridentate thiols, oligopeptides (e.g., dipeptides), amine or carboxylic acid containing organic molecules (e.g., HDA), functionalized organophosphorous compounds (e.g., phosphonic acids, phosphinic acids), hydrophilic phosphonic acids, or hydrophilic phosphine oligimers.

Also provided herein are compositions that include the disclosed nanocrystal(s). Thus, in another aspect, colloidal dispersions of semiconductor nanocrystals are provided herein. The dispersion can include a population of semiconductor nanocrystals and an aqueous (e.g., water, serum, or buffer) or organic medium (e.g., a polymer or an organic solvent such as hexane, toluene, chloroform, decane, and the like). In certain embodiments, the nanocrystals disclosed herein are provided in polymeric medium or matrix. In certain embodiments, the disclosed nanocrystals are provided as part of a photovoltaic or light-emitting device or as a component in a fluorescent ink.

For certain applications, it may be desirable to attach an affinity molecule to the nanocrystal surface. For example, the nanocrystal can include a surface coating capable of linking to an affinity molecule, such as a biological molecule. Biological affinity molecules include, for example, nucleic acids, oligonucleotides, nucleotides, proteins, antibodies, peptides, lipids, carbohydrates, and the like). Thus, in another aspect, a population of nanocrystals is provided, wherein each nanocrystal further comprises a plurality of linking agents capable of linking the nanocrystals to affinity molecules.

In certain embodiments, the nanocrystals disclosed herein are associated with a cell, drug, phospholipid or micelle. Thus, in one aspect is provided a population of nanocrystals, wherein each nanocrystal in the population is associated or linked to a biological molecule, cell, or drug. In certain embodiments, the nanocrystal can be encapsulated within a micelle or phospholipid coating or can be attached to or contained within a cell (e.g., in the cytoplasm, an organelle, a cellular membrane, the cell nucleus, etc.).

The nanocrystals described herein also can be part of a kit. Kits for various biological applications are provided herein (e.g., cellular labeling). Thus, in another aspect is provided a kit for labeling cells with a population of nanocrystals, comprising:
  a) an aqueous dispersion of nanocrystals, as disclosed herein; and optionally
  b) instructions for labeling cells with the population of nanocrystals.

Also provided herein are methods of using the disclosed nanocrystals. The disclosed nanocrystals can be used for biological or non-biological applications. For example, a method of identifying a sample is provided in which a population of semiconductor nanocrystals is contacted with a cell, tissue, or biological molecule. During or after contact, the nanocrystal is excited with light and the fluorescence emission of the semiconductor nanocrystals is detected (e.g., by imaging or flow cytometry).

The semiconductor nanocrystal-based materials provided herein offer numerous advantages over traditional core-shell semiconductor nanocrystal materials, since these nanocrystals have high quantum yields in both organic and aqueous media. These properties make these materials particularly useful for biological applications carried out in aqueous environments.

The following examples are offered to illustrate but not to limit the embodiments described herein.

EXAMPLES

Example 1

Preparation of Core-Shell Nanocrystals Using Mixtures of EPA and TDPA

Core-shell nanocrystals were prepared from non-spherical CdSe and CdSeTe cores in the presence of different ratios of EPA:TDPA. CdSe and CdSeTe cores were prepared as described in U.S. Pat. Nos. 7,147,712 or 7,695,642. A 1:1 (weight:volume) mixture of tri-n-octylphosphine oxide (TOPO) and tri-n-octylphosphine (TOP) was introduced into a flask. Tetradecylphosphonic acid (TDPA) and ethylphosphonic acid (EPA) were added to the flask in an amount suitable to fully passivate the final materials, as can be calculated from the reaction scale and the expected final nanoparticle size. The mole fraction of EPA relative to the total amount of oxoacid was varied over a range of values to prepare a series of core-shell nanocrystals. The contents of the flask were heated under vacuum and then the flask was refilled with $N_2$ and cooled.

A solution of a suitable cadmium precursor (such as dimethylcadmium or cadmium acetate) in TOP was prepared in a glove box in a quantity sufficient to produce a desired thickness of shell, as can be calculated by one of ordinary skill in the art. Separately, a solution of a suitable sulfur precursor (such as trimethylsilylsulfide [$(TMS)_2S$], elemental sulfur) and zinc precursor (such as diethyl zinc ($Et_2Zn$) or zinc stearate) was prepared in TOP in a quantity sufficient to produce a desired shell thickness. Each of these solutions was taken up in separate syringes and removed from the glove box.

108.5 mL (at an optical density of 15.55 at 550 nm) of a core/hexane solution was added to the reaction flask and the hexane was removed by vacuum; the flask was then refilled with nitrogen. The flask was heated to the desired synthesis temperature, typically about 150° C. to about 250° C. The two shell precursor solutions were then added in layer additions to produce the desired thickness of shell. The amount of shell precursors added was based upon the starting size of the underlying cores. As each layer of shell material was added, a new "core" size was determined by taking the previous "core" size and adding to it the thickness of just-added shell material. Using this approach, a slightly larger volume of the following shell material needed to be added for each subsequent layer of shell material. After the desired thickness of shell material was added, the reaction flask was cooled, and the product was isolated by conventional methods. Table 1 shows the effect of using mixtures of EPA and TDPA on the optical properties of various types of core/shell nanocrystal materials prepared as described herein.

TABLE 1

Effect of mixtures of EPA and TDPA on optical properties

| core composition | mole fraction EPA | emission wavelength (nm) | QY in hexane (%) | QY in water (%) |
|---|---|---|---|---|
| CdSe | 0 | 649 | 73 | 65 |
| CdSe | 3 | 652 | 82 | 82 |
| CdSe | 7 | 656 | 86 | 78 |
| CdSe | 10 | 658 | 87 | 78 |
| CdSeTe | 0 | 701 | 81 | 76 |
| CdSeTe | 3 | 704 | 84 | 81 |
| CdSeTe | 7 | 702 | 88 | 77 |
| CdSeTe | 10 | 705 | 87 | 82 |

Example 2

Preparation of Core-Shell Nanocrystals Using a Mixture of BPA and TDPA

Core-shell nanocrystals were prepared from non-spherical CdSe cores in the presence of a mixture of butylphosphonic acid (BPA) and TDPA. CdSe cores were prepared as described as in Example 1. A 1:1 (weight:volume) mixture of tri-n-octylphosphine oxide (TOPO) and tri-n-octylphosphine (TOP) was introduced into a flask. TDPA and BPA were added to the flask in an amount suitable to fully passivate the final materials, as can be calculated from the reaction scale and the expected final nanoparticle size. The calculated mole fraction of BPA relative to the total amount of oxoacid was 10 percent. The contents of the flask were heated under vacuum and then the flask was refilled with $N_2$ and cooled. Solutions of cadmium precursor, sulfur precursor and zinc precursor were prepared in TOP as described in Example 1.

119.7 mL (at an optical density of 14.1 at 550 nm) of a core/hexane solution was added to the reaction flask and the hexane was removed by vacuum; the flask was then refilled with nitrogen. The flask was heated to the desired synthesis temperature, typically about 150° C. to about 250° C. The two shell precursor solutions were then added in layer additions as described in Example 1 to produce the desired thickness of shell. After the desired thickness of shell material was added, the reaction flask was cooled, and the product was isolated by conventional methods. The emission of maximum of the core-shell nanocrystals was 654.7 nm with a full width at half maximum (FWHM) of 27.1 nm. The quantum yield was 82.8%.

Example 3

Preparation of Core-Shell Nanocrystals Using a Mixture of HPA and TDPA

Core-shell nanocrystals were prepared from non-spherical CdSe cores in a mixture of hexylphosphonic acid (HPA) and TDPA. CdSe cores were prepared as described in Example 1. A 1:1 (weight:volume) mixture of tri-n-octylphosphine oxide (TOPO) and tri-n-octylphosphine (TOP) was introduced into a flask. Tetredecylphosphonic acid (TDPA) and hexylphosphonic acid (HPA) were added to the flask in an amount suitable to fully passivate the final materials, as can be calculated from the reaction scale and the expected final nanoparticle size. The mole fraction of HPA relative to the total amount of oxoacid was 10 percent. The contents of the flask were heated under vacuum and then the flask was refilled with $N_2$ and cooled. Solutions of cadmium precursor, sulfur precursor and zinc precursor were prepared in TOP as described in Example 1.

21.7 mL (at an optical density of 11.5 at 550 nm) of a core/hexane solution was added to the reaction flask and the hexane was removed by vacuum; the flask was then refilled with nitrogen. The flask was heated to the desired synthesis temperature, typically about 150° C. to about 250° C. The two shell precursor solutions were then added in layer additions to produce the desired thickness of shell as described in Example 1. After the desired thickness of shell material was added, the reaction flask was cooled, and the product was isolated by conventional methods. The emission of maximum of the core-shell nanocrystals was 649.7 nm with a full width at half maximum (FWHM) of 24.6 nm. The quantum yield was 78%.

Example 4

Preparation of Core-Shell Nanocrystals Using a Mixture of EPA and TDPA

Core-shell nanocrystals were prepared from nearly spherical CdSe cores in a mixture of EPA and TDPA. CdSe cores were prepared as described in Example 1. A 1:1 (weight:volume) mixture of tri-n-octylphosphine oxide (TOPO) and tri-n-octylphosphine (TOP) was introduced into a flask. Tetredecylphosphonic acid (TDPA) and ethylphosphonic acid (EPA) were added to the flask in an amount suitable to fully passivate the final materials, as can be calculated from the reaction scale and the expected final nanoparticle size. The mole fraction of EPA relative to the total amount of oxoacid was 10 percent. The contents of the flask were heated under vacuum and then the flask was refilled with $N_2$ and cooled. Solutions of cadmium precursor, sulfur precursor and zinc precursor were prepared in TOP as described in Example 1.

16.4 mL (at an optical density of 34.4 at 550 nm) of a core/hexane solution was added to the reaction flask and the hexane was removed by vacuum; the flask was then refilled with nitrogen. The flask was heated to the desired synthesis temperature, typically about 150° C. to about 250° C. The two shell precursor solutions were then added in layer additions as described in Example 1 to produce the desired thickness of shell. After the desired thickness of shell material was added, the reaction flask was cooled, and the product was isolated by conventional methods. The emission maximum of the core-shell nanocrystals was 584.6 nm with a full width at half maximum (FWHM) of 30.9 nm. The quantum yield was 80%.

Example 5

TEM Analysis of Nanocrystals

Figure 2A:
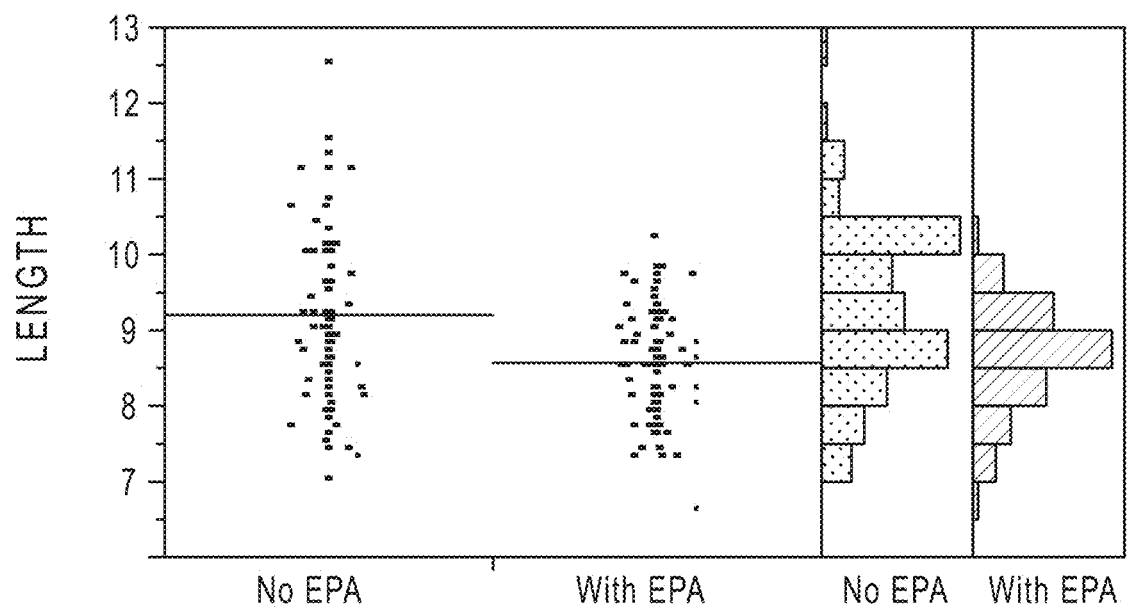
FIG. 2A is a graphical representation of the statistical analysis performed on TEM particle sizing data for nanocrystal core-shells synthesized with a mixture of oxoacid compounds.
Figure 2B:
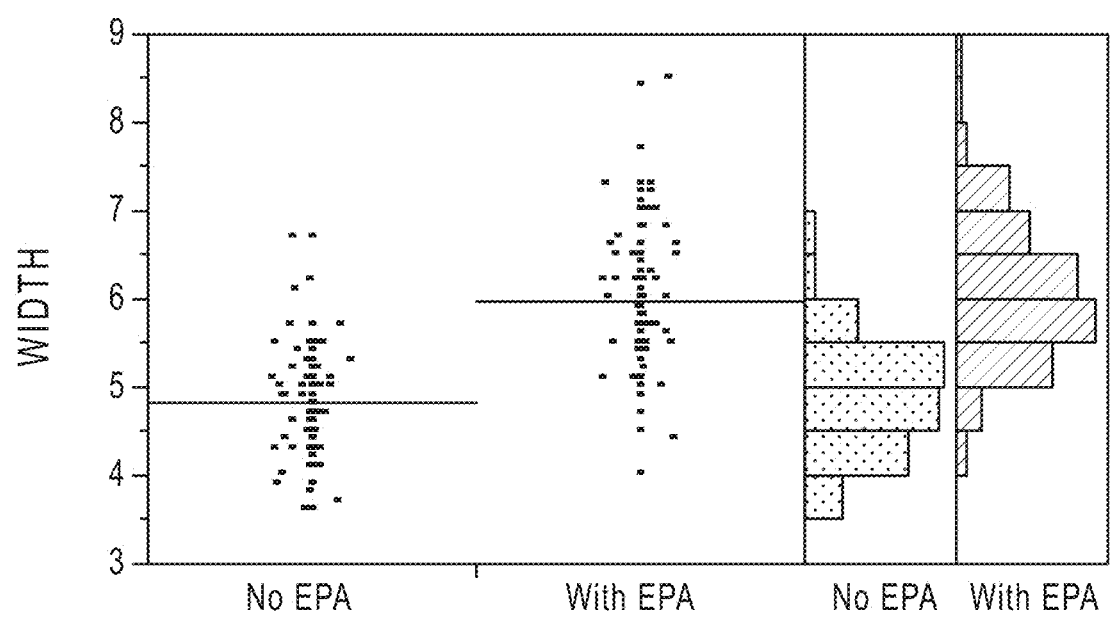
FIG. 2B is a graphical representation of the statistical analysis performed on TEM particle sizing data for nanocrystal core-shells synthesized without a mixture of oxoacid compounds.
Figure 3A:
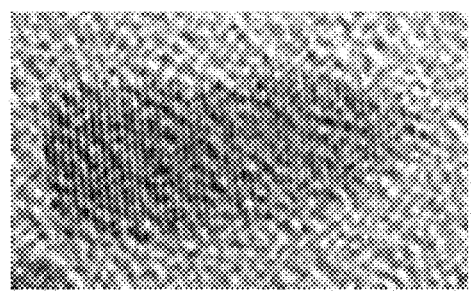
FIG. 3A shows TEM micrographs of a nanocrystal core-shell synthesized using standard methods.
Figure 3B:
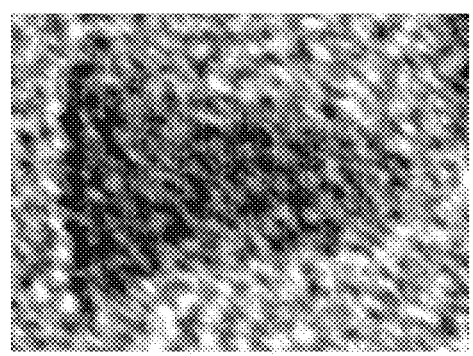
FIG. 3B shows TEM micrograph of a nanocrystal core-shell synthesized using a mixture of oxoacid compounds.

The nanocrystals prepared in Example 1 were analyzed using transmission electron microscopy (TEM) to determine the effect of EPA on the dimensions of the nanocrystals. TEM was performed on a JEOL 200cx in brightfield mode at 200,000 magnification. Particle sizing was performed by hand using ImageJ image analysis software. Statistical data analysis was performed using JMP® statistical software. The output of the JMP statistical analysis is shown graphically in FIG. 2A and FIG. 2B. Representative single particle TEM images for the samples prepared with and without EPA are shown in FIG. 3A and FIG. 3B. For each analysis, at least 100 particles were measured, data tested for normality and probabilities calculated to determine whether there was a statistical difference. Differences were considered significant if the probability (p-value) associated with a student's paired t-test, with a two-tailed distribution was less than 0.01. The x-y plot on the left shows the length and width in nanometers for each particle and the mean for each population as a horizontal line. The plot on the right shows the histograms for both length and width. Comparing the two sets of data reveals that EPA has the effect of increasing the width (p-value=$7.3 \times 10^{-20}$) of the particle and decreasing the length (p-value=$3.7 \times 10^{-6}$) of the particle. This demonstrates that a mixture of two different phosphonic acid compounds can be used in the described method to differentially deposit shell material along the shorter axes of the nanocrystal core, and thereby making the shell thickness more uniform over the core.

Example 6

Optical Properties of Nanocrystals

Optical properties of a series of core-shell nanocrystals prepared according to the procedures described in Example 1 were measured in organic and aqueous media. For measurement in organic media, nanocrystals were suspended in hexane at an optical density of 0.025 at 550 nm and excited with 365 nm light. For measurement in aqueous media, nanocrystals were further treated with an amphiphilic polymer to render them water-dispersible.

Absolute quantum yield was measured on a Hamamatsu Absolute PL Quantum Yield Measurement System (model C9920-02). Crude core-shell solutions were first precipitated with 1 equivalent of a mixture of 75:25 methanol:isopropyl alcohol. To the precipitate, 1 equivalent of hexane was added and insoluble materials were removed by either filtration or centrifugation. Organic soluble samples were further diluted with hexane to an optical density of 0.03 at 530 nm prior to measurement. Aqueous samples were diluted with DI water to the same optical density as above.

Figure 4:
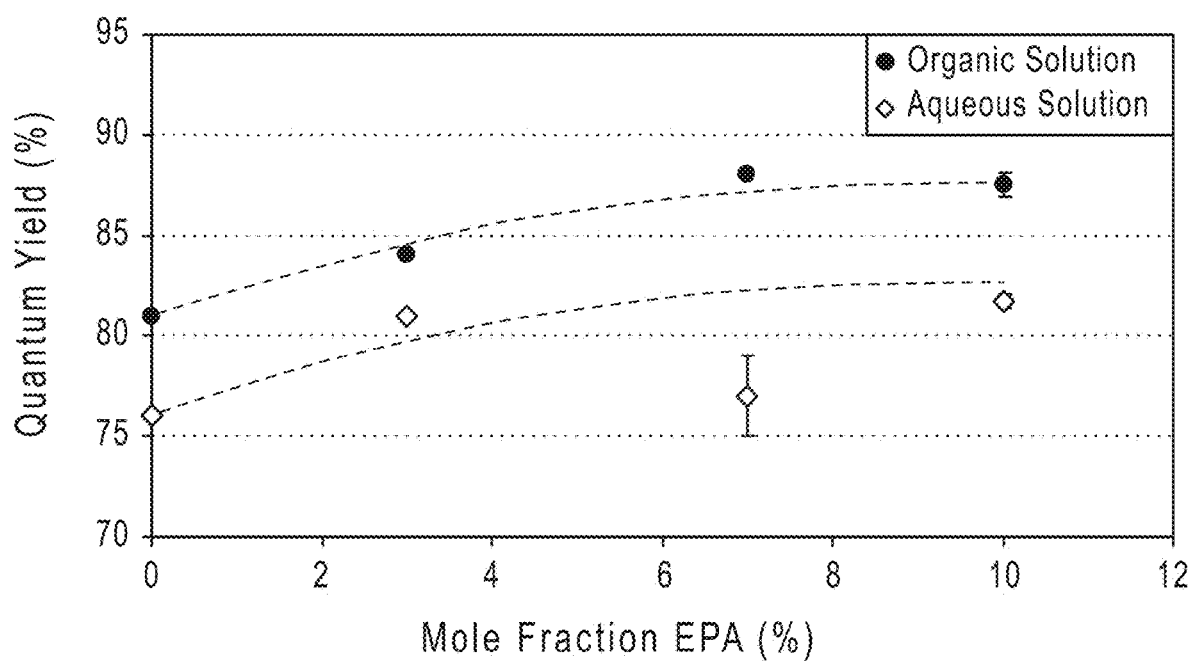
FIG. 4 is a plot showing the effect of adjusting the mole fraction of EPA on quantum yield for a population of quantum dots (maximum emission wavelength ~705 nm) in organic (circle) and aqueous (diamond) solutions.
Figure 5:
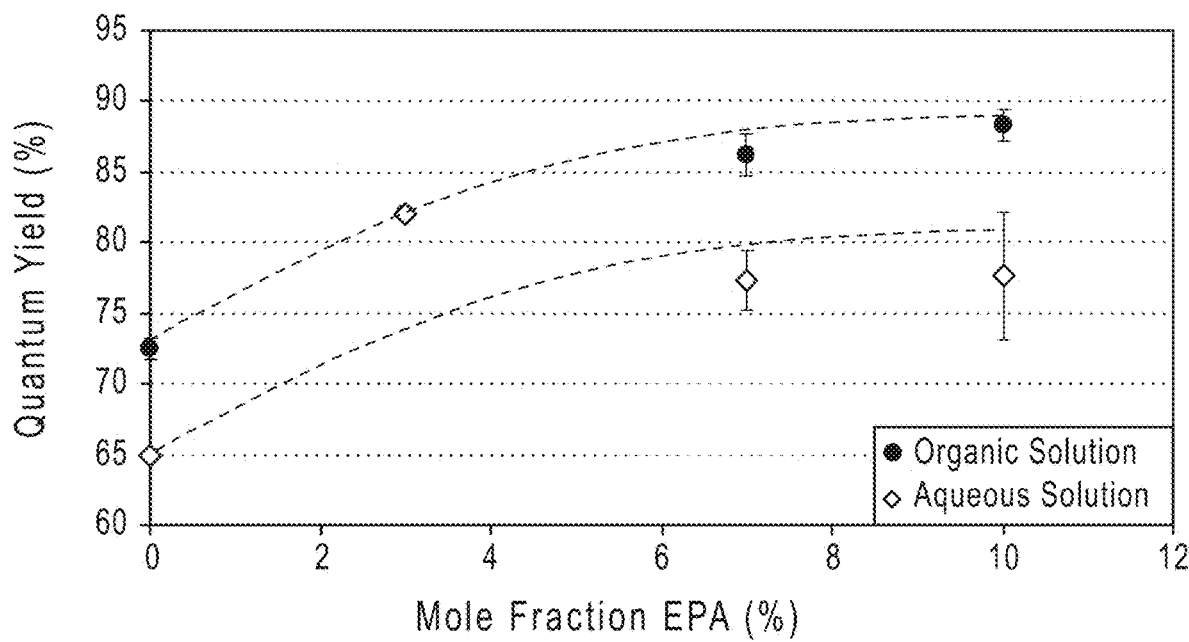
FIG. 5 is a plot showing the effect of adjusting the mole fraction of EPA on quantum yield for a population of quantum dots (maximum emission wavelength ~655 nm) in organic (circle) and aqueous (diamond) solutions.
Figure 6:
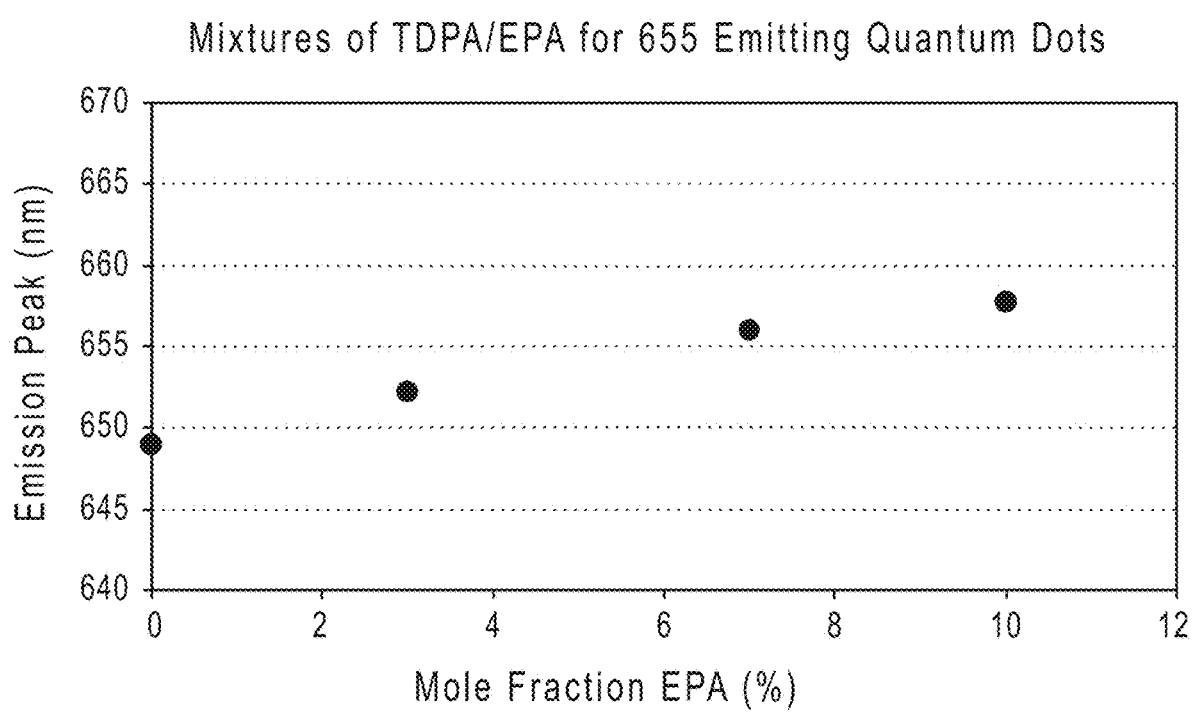
FIG. 6 is a plot showing the effect of increasing the mole fraction of EPA on emission peak for a population of quantum dots (maximum emission wavelength ~655 nm).

As the mole ratio of EPA (relative to TDPA) was increased, a corresponding increase in quantum yield was observed in both aqueous and organic media (FIG. 4 and FIG. 5). In addition, the emission wavelength of the nanocrystals was shifted to longer wavelengths (red-shifting) with increasing mole ratio of the lower molecular weight phosphonic acid (FIG. 6). Without wishing to be bound by theory, this trend appears consistent with the observations described in Example 2. As observed under TEM, when shell is deposited differentially along the x and y axis of an elongated particle, the particle becomes less elongated. It is known that the emission wavelength of a non-spherical semiconductor nanocrystal is typically dictated by the dimensions of the shortest axis. A larger, spherical particle would be expected to exhibit a longer emission wavelength due to a reduction in quantum confinement. Thus, in the present method, as the aspect ratio of particle decreases and the particle becomes more spherical, fluorescence emission would be expected to shift to longer wavelengths. The red-shift observed with increasing mole ratio of a lower molecular weight phosphonic acid used in the described method is consistent with production of a more spherical nanocrystal resulting from differential deposition of shell along the shorter axes of the nanocrystal core.

The foregoing examples illustrate various aspects of the invention and are not intended to provide an exhaustive description of the many different possible embodiments of the invention. Thus, those of ordinary skill in the art will realize readily that many changes and modifications can be made thereto without departing from the spirit or scope of the appended claims and their equivalents.

What is claimed is:

1. A method for producing a population of semiconductor nanocrystals, comprising:
    combining a plurality of elongated semiconductor nanocrystal cores, at least one solvent, a first semiconductor shell precursor, and a second semiconductor shell precursor, wherein the first and second semiconductor shell precursors are different, and at least two different oxoacid compounds to provide a reaction mixture, wherein the at least two different oxoacid compounds comprise a first oxoacid compound and a second oxoacid compound, wherein the first and second oxoacid compounds have different molecular weights, wherein the mole fraction of the lower molecular weight oxoacid compound relative to the total number of moles of oxoacid compounds is about 0.5% to about 20%; and
    heating the reaction mixture for a period of time sufficient to induce formation of a semiconductor shell layer on at least one core, thereby producing a population of semiconductor nanocrystals, wherein each nanocrystal core has a first aspect ratio and each semiconductor core-shell nanocrystal has a second aspect ratio, wherein the second aspect ratio is less than the first aspect ratio,
    wherein the at least two oxoacid compounds comprise a first compound selected from $C_1$-$C_{10}$ alkylphosphonic acid compounds and a second compound selected from $C_{10}$-$C_{20}$ alkylphosphonic acid compounds.

2. The method of claim 1, further comprising:
    first combining the plurality of semiconductor nanocrystal cores with the at least one solvent and the at least two different oxoacid compounds; and
    then adding the first and second semiconductor shell precursors.

3. The method of claim 1, further comprising:
    first combining the plurality of semiconductor nanocrystal cores with the at least one solvent; and
    then adding the first and second semiconductor shell precursors and the at least two different oxoacid compounds.

4. The method of claim 1, wherein the first and second shell precursors are added alternately in layer additions.

5. The method of claim 1, wherein at least one oxoacid compound is methylphosphonic acid, ethylphosphonic acid, butylphosphonic acid, hexylphosphonic acid, or octylphosphonic acid.

6. The method of claim 1, wherein at least one oxoacid compound is tetradecylphosphonic acid.

7. A method for producing a population of semiconductor nanocrystals, comprising:
    combining a plurality of elongated semiconductor nanocrystal cores, at least one solvent, a first semiconductor shell precursor, and a second semiconductor shell precursor, wherein the first and second semiconductor shell precursors are different, and at least two different oxoacid compounds to provide a reaction mixture, wherein the at least two different oxoacid compounds comprise a first oxoacid compound and a second oxoacid compound, wherein the first and second oxoacid compounds have different molecular weights, wherein the mole fraction of the lower molecular weight oxoacid compound relative to the total number of moles of oxoacid compounds is about 0.5% to about 20%; and
    heating the reaction mixture for a period of time sufficient to induce formation of a semiconductor shell layer on at least one core, thereby producing a population of semiconductor nanocrystals, wherein each nanocrystal core has a first aspect ratio and each semiconductor core-shell nanocrystal has a second aspect ratio, wherein the second aspect ratio is less than the first aspect ratio,
    wherein the at least two oxoacid compounds comprise tetradecylphosphonic acid and ethylphosphonic acid.

8. A method for producing a population of semiconductor nanocrystals, comprising:
    combining a plurality of elongated semiconductor nanocrystal cores, at least one solvent, a first semiconductor shell precursor, and a second semiconductor shell precursor, wherein the first and second semiconductor shell precursors are different, and at least two different oxoacid compounds to provide a reaction mixture, wherein the at least two different oxoacid compounds comprise a first oxoacid compound and a second oxoacid compound, wherein the first and second oxoacid compounds have different molecular weights, wherein the mole fraction of the lower molecular weight oxoacid compound relative to the total number of moles of oxoacid compounds is about 0.5% to about 20%; and
    heating the reaction mixture for a period of time sufficient to induce formation of a semiconductor shell layer on at least one core, thereby producing a population of semiconductor nanocrystals, wherein each nanocrystal core has a first aspect ratio and each semiconductor core-shell nanocrystal has a second aspect ratio, wherein the second aspect ratio is less than the first aspect ratio,
    wherein the at least two different oxoacid compounds comprise a first compound selected from the group consisting of $C_{10}$-$C_{20}$ carboxylic acids and a second compound selected from $C_1$-$C_{10}$ carboxylic acids.

9. The method of claim 8, wherein at least one of the two different oxoacid compounds is selected from the group consisting of lauric acid, myristic acid, palmitic acid, and stearic acid, and at least one of the two different oxoacid compounds is selected from the group consisting of acetic acid, propionic acid, butyric acid, hexanoic acid, and octanoic acid.

10. The method of claim 1, wherein the first semiconductor shell precursor is selected from the group consisting of Group 2, 12, 13 and 14 element-containing compounds.

11. The method of claim 1, wherein the second semiconductor shell precursor is selected from the group consisting of Group 2, 12, 13, 14, 15 and 16 element-containing compounds.

12. The method of claim 7, wherein the first semiconductor shell precursor is selected from the group consisting of Group 2, 12, 13 and 14 element-containing compounds.

13. The method of claim 7, wherein the second semiconductor shell precursor is selected from the group consisting of Group 2, 12, 13, 14, 15 and 16 element-containing compounds.

14. The method of claim 8, wherein the first semiconductor shell precursor is selected from the group consisting of Group 2, 12, 13 and 14 element-containing compounds.

15. The method of claim 8, wherein the second semiconductor shell precursor is selected from the group consisting of Group 2, 12, 13, 14, 15 and 16 element-containing compounds.

* * * * *

UNITED STATES PATENT AND TRADEMARK OFFICE
CERTIFICATE OF CORRECTION

PATENT NO. : 11,011,603 B2
APPLICATION NO. : 16/107903
DATED : May 18, 2021
INVENTOR(S) : Joseph Bartel Page 1 of 1

It is certified that error appears in the above-identified patent and that said Letters Patent is hereby corrected as shown below:

On the Title Page

In Column 1, item (72), under First Inventor, Line 1, delete "Joseph Bartel" and insert -- Joseph August Bartel --, therefor.

In Column 1, item (72), under Fifth Inventor, Line 5, delete "Scott Sweeney" and insert -- Scott F. Sweeney --, therefor.

In Column 1, item (72), under Sixth Inventor, Line 6, delete "Chad Teters" and insert -- Chad N. Teters --, therefor.

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*